(12) United States Patent
Zhao et al.

(10) Patent No.: US 12,128,084 B2
(45) Date of Patent: Oct. 29, 2024

(54) USE OF PAYCS IN REGULATION OF INTESTINAL FLORA, METABOLITES, AND BRAIN NEUROTRANSMITTERS

(71) Applicant: Sericulture and Agri-Food Research Institute, Guangdong Academy of Agricultural Sciences, Guangzhou (CN)

(72) Inventors: Tiantian Zhao, Guangzhou (CN); Yehui Zhang, Guangzhou (CN); Yousheng Zhang, Guangzhou (CN); Wenjuan Jiao, Guangzhou (CN); Weifeng Liu, Guangzhou (CN); Shuai Chen, Guangzhou (CN)

(73) Assignee: Sericulture and Agri-Food Research Institute, Guangdong Academy of Agricultural Sciences, Guangzhou (CN)

( * ) Notice: Subject to any disclaimer, the term of this patent is extended or adjusted under 35 U.S.C. 154(b) by 0 days.

(21) Appl. No.: 18/170,163

(22) Filed: Feb. 16, 2023

(65) Prior Publication Data
US 2023/0330177 A1    Oct. 19, 2023

(30) Foreign Application Priority Data
Feb. 17, 2022   (CN) .......................... 202210147703.1

(51) Int. Cl.
| | |
|---|---|
| *A61K 38/08* | (2019.01) |
| *A61P 1/14* | (2006.01) |
| *A61P 25/28* | (2006.01) |
| *A61P 29/00* | (2006.01) |
| *C12P 21/06* | (2006.01) |

(52) U.S. Cl.
CPC .............. *A61K 38/08* (2013.01); *A61P 1/14* (2018.01); *A61P 25/28* (2018.01); *A61P 29/00* (2018.01); *C12P 21/06* (2013.01)

(58) Field of Classification Search
None
See application file for complete search history.

(56) References Cited

PUBLICATIONS

Zhao, Tiantian "Study on the Memory Improving Effects of Peptides Derived from Anchovy on Scopolamine-Induced Amnesia Mice" Chinese Doctoral Dissertations Full-text Database Engineering Science and Technology, South China University of Technology (Guangzhou, China), Apr. 2018, pp. 1-150.
Office Action for CN 202210147703.1 issued Oct. 19, 2022.

*Primary Examiner* — Sergio Coffa
(74) *Attorney, Agent, or Firm* — Gearhart Law, LLC

(57) ABSTRACT

The present disclosure belongs to the technical field of health food, and in particular, relates to the use of PAYCS in the regulation of intestinal flora, metabolites, and brain neurotransmitters. PAYCS remedies scopolamine-induced memory impairment in mice through target oxidation, inflammatory stress and regulation of the intestinal microorganism-metabolite-brain neurotransmitter axis through PAYCS. PAYCS improves the memory pathway through the intestinal microorganism-metabolite-neurotransmitter axis. PAYCS can significantly reduce serum MDA and LDH levels and significantly increase liver SOD content. PAYCS-H inhibits the increase of liver TNF-$\alpha$ and IL-1$\beta$, while PAYCS-L can only reduce the content of TNF-$\alpha$ in the liver. Thus, PAYCS-L changes the ratio of *Bacteroides/Firmicutes* and increases the relative abundance of plants such as Cactaceae and Prevotellaceae, improving the neurotransmitters associated with the metabolism of tryptophan in the brain.

6 Claims, 40 Drawing Sheets
Specification includes a Sequence Listing.

5BY1- Blume a la ctone C
5BY2- Tha lictroidine
5BY3- Notogins enoside M
5BY4- 3a ,7a ,12b-Trihydroxy-5b-cholanoic a cid
5BY5- Sequite rpene La ctone 326
5BY6- He lena lin
5BY7- Gamma -CEHC
5BY8- Ma ra smone
5BY9- 2-Deoxyga la ctopyranos e
5BY10- AMINOHYDROXYBUTYRIC ACID
5BY11- 5'-Deoxy-5'-<WBR>(me thylthio)adenosine
5BY12- Dynorphin B (6-9)
5BY13- L-Proline
5BY14- Glabrin D
5BY15- Lysyl-Hydroxyproline
5BY16- Dihydrodigoxin
5BY17- Aspa raginyl-Isoleucine
5BY18- Gamma -Glutamylva line
5BY19- N(6)-Me thyllysine
5BY20- Threoninyl-Va line
5BY21- Ornithine
5BY22- L-Arginine
5BY23- 2-Hydroxycinnamic a cid
5BY24- Spe rmidine
5BY25- Spe rmidine
5BY26- Citrulline
5BY27- D-Pipe colic a cid
5BY28- L-Histidine
5BY29- Alanyl-Se rine
5BY30- (1be ta ,2a lpha ,3a lpha )-1,2,3,24-Te trahydroxy-12-ole anen-28-oic a cid
5BY31- Dode canol
5BY32- Isoleucyl-Isoleucine
5BY33- Cyclo(Leu-Phe )
5BY34- ALANYL-dl-LEUCINE
5BY35- Alanyl-Va line
5BY36- Isoleucyl-Va line
5BY37- Cholic a cid
5BY38- Isoleucyl-Glutamine
5BY39- Cyclotricuspidoside C
5BY40- 2,3-Dihydro-6-me thyl-5-(5-me thyl-2-furanyl)-1H-pyrrolizine
5BY41- 1-Ste a roylglyce rophosphoinositol
5BY42- Be ta -Elemolic a cid
5BY43- Cholic a cid glucuronide
5BY44- 1a lpha ,24-Dihydroxy-22-ene -24-cyclopropylvitamin D3
5BY45- Muricore a cin
5BY46- 23-Ace toxysoladulcidine
5BY47- Cis-3-Hexenyl pentanoa te
5BY48- Ganolucidic a cid D
5BY49- Frangulanine
5BY50- Pona ste roside A

FIG. 5B (con't)

10AX1 s__Staphylococcus_lentus_g__Staphylococcus
10AX2 s__unclassified_g__Ruminococcus_1
10AX3 s__unidentified_rumen_bacterium_JW32
10AX4 s__uncultured_bacterium_g__Lachnospiraceae_NK4A136_group
10AX5 s__[Clostridium]_leptum_g__Oscillibacter
10AX6 s__uncultured_bacterium_g__Parasutterella
10AX7 s__unclassified_g__Parabacteroides
10AX8 s__uncultured_bacterium_g__Muribaculum
10AX9 s__unclassified_g__norank_f__Muribaculaceae
10AX10 s__unclassified_g__Bacteroides
10AX11 s__uncultured_bacterium_g__Alistipes
10AX12 s__uncultured_bacterium_g__Prevotellaceae_UCG-001
10AX13 s__Bacteroides_caecimuris
10AX14 s__Aerococcus_viridans
10AX15 s__Corynebacterium_stationis
10AX16 s__uncultured_Bacteroidales_bacterium_g__Alloprevotella
10AX17 s__unclassified_o__Bacteroidales
10AX18 s__Bacteroides_acidifaciens
10AX19 s__uncultured_organism_g__Parabacteroides
10AX20 s__uncultured_bacterium_g__Ruminococcaceae_UCG-014
10AX21 s__uncultured_organism_g__[Eubacterium]_ventriosum_group
10AX22 s__Lachnospiraceae_bacterium_A4
10AX23 s__unclassified_g__Lachnospiraceae_NK4A136_group
10AX24 s__uncultured_bacterium_g__Oscillibacter
10AX25 s__uncultured_Clostridiales_bacterium_g__Lachnospiraceae_NK4A136_group
10AX26 s__uncultured_bacterium_g__Candidatus_Saccharimonas
10AX27 s__unclassified_g__Akkermansia
10AX28 s__unclassified_f__Lachnospiraceae
10AX29 s__uncultured_bacterium_g__Lachnoclostridium
10AX30 s__unclassified_g__Roseburia
10AX31 s__unclassified_g__norank_f__Ruminococcaceae
10AX32 s__unclassified_g__Lachnoclostridium
10AX33 s__uncultured_Bacteroidales_bacterium_g__norank_f__Muribaculaceae
10AX34 s__unclassified_g__Ruminococcaceae_UCG-014
10AX35 s__Bifidobacterium_pseudolongum_PV8-2
10AX36 s__Bacteroides_sartorii
10AX37 s__uncultured_bacterium_g__[Eubacterium]_xylanophilum_group
10AX38 s__unclassified_g__norank_f__Lachnospiraceae
10AX39 s__uncultured_bacterium_g__norank_f__Desulfovibrionaceae
10AX40 s__unclassified_g__Ruminiclostridium_9
10AX41 s__uncultured_bacterium_g__norank_f__Lachnospiraceae
10AX42 s__uncultured_bacterium_g__Ruminiclostridium
10AX43 s__unclassified_f__Ruminococcaceae
10AX44 s__uncultured_bacterium_g__Faecalibaculum
10AX45 s__unclassified_g__Lactobacillus
10AX46 s__Lactobacillus_reuteri
10AX47 s__unclassified_g__Helicobacter
10AX48 s__Helicobacter_ganmani
10AX49 s__uncultured_bacterium_g__norank_f__Muribaculaceae
10AX50 s__uncultured_bacterium_g__Enterorhabdus

FIG. 10A (con't)

10AY1 Pregnan-20-one,17-(acetyloxy)-3-hydroxy-6-methyl-,(3b,5b,6a)-
10AY2 Adhumulone
2-Deoxygalactopyranose
10AY3 PC(16:0/0:0)[U]
10AY4 PC(16:0/0:0)[U]
10AY5 3a,7a,12b-Trihydroxy-5b-cholanoic acid
10AY6 A-L-Arabinofuranosyl-(1->2)-[a-D-mannopyranosyl-(1->6)]-
10AY7 D-mannose
10AY8 7-dehydrocholesterol
10AY9 Sophoraflavanone B
10AY10 Ganosporelactone A
10AY11 24S-OH-7-DHC
10AY12 Choline
10AY13 Vinaginsenoside R14
10AY14 13(S)-HpOTrE
10AY15 4-ene-Valproic acid
10AY16 Phaseolic acid
10AY17 Ciclesonide
10AY18 Homoveratric acid
10AY19 (±)13-HpODE
10AY20 Floionolic acid
10AY21 LysoPE(16:1(9Z)/0:0)
10AY22 3-Hydroxy-4,6-heptadiyne-1-yl 1-glucoside
10AY23 Momordol
10AY24 Acetoxy-8-gingerol
10AY25 (±)12,13-DiHOME
10AY26 Gamma-Tocotrienol
10AY27 PG(16:0/0:0)[U]
10AY28 PG(18:1(9Z)/0:0)
10AY29 (±)9-HpODE
10AY30 19-Norandrosterone
10AY31 5-cis Carbaprostacyclin
10AY32 Diosmin
10AY33 N-Acetylgalactosamine
10AY34 Deoxypyridinoline
10AY35 4-Hydroxyproline galactoside
10AY36 (1S,2S,4S,5R)-1,8-Epoxy-p-menthane-2,5-diol
10AY37 23-Acetoxysoladulcidine
10AY38 (20S)-1alpha,20,25-trihydroxy-26,27-dimethyl-24a-homovitamin D3
10AY39 7S,8S-DiHOTrE
10AY40 Alpha-(Methylenecyclopropyl)glycine
10AY41 Spirolide E
10AY42 L-a-Lysophosphatidylserine
10AY43 Ricinoleic Acid methyl ester
10AY44 Pantothenic Acid
10AY45 Thymine
10AY46 Linoelaidic Acid
10AY47 9,10-epoxy-12-octadecenoic acid
10AY48 Sorbitan laurate
10AY49 Kynurenic acid
10AY50 Glycyl-Phenylalanine

FIG. 10A (con't)

10BX1- s__unclassified_g__Mucispirillum
10BX2- s__Lactobacillus_reuteri
10BX3- s__uncultured_bacterium_g__norank_f__norank_o__Mollicutes_RF39
10BX4- s__uncultured_rumen_bacterium_g__Ruminococcaceae_UCG-014
10BX5- s__unclassified_f__Lachnospiraceae
10BX6- s__uncultured_bacterium_g__norank_f__Desulfovibrionaceae
10BX7- s__uncultured_bacterium_g__norank_f__Lachnospiraceae
10BX8- s__uncultured_bacterium_g__Alistipe
10BX9- s__uncultured_bacterium_g__Candidatus_Saccharimonas
10BX10- s__unclassified_g__Bacteroides
10BX11- s__unclassified_g__Lactobacillus
10BX12- s__unclassified_g__Parabacteroides
10BX13- s__unclassified_g__Akkermansia
10BX14- s__uncultured_Bacteroidales_bacterium_g__Alloprevotella
10BX15- s__uncultured_bacterium_g__[Eubacterium]_xylanophilum_group
10BX16- s__uncultured_Clostridiales_bacterium_g__Lachnospiraceae_NK4A136_group
10BX17- s__unclassified_g__norank_f__Ruminococcaceae
10BX18- s__uncultured_bacterium_g__Ruminiclostridium
10BX19- s__Lachnospiraceae_bacterium_A4
10BX20- s__unclassified_g__norank_f__Peptococcaceae
10BX21- s__unclassified_f__Ruminococcaceae
10BX22- s__uncultured_bacterium_g__Oscillibacter
10BX23- s__unclassified_g__Ruminiclostridium_9
10BX24- s__unclassified_g__Lachnospiraceae_NK4A136_group
10BX25- s__Ruminiclostridium_sp._KB18
10BX26- s__unclassified_g__Ruminococcaceae_UCG-014
10BX27- s__Bacteroides_sartor
10BX28- s__uncultured_bacterium_g__Ruminococcaceae_UCG-014
10BX29- s__Bacteroides_acidifaciens
10BX30- s__uncultured_organism_g__Parabacteroides
10BX31- s__Bacteroides_caecimuris
10BX32- s__uncultured_bacterium_g__Parasutterella
10BX33- s__unclassified_o__Bacteroidales
10BX34- s__uncultured_bacterium_g__Enterorhabdus
10BX35- s__unclassified_g__norank_f__Lachnospiraceae
10BX36- s__[Clostridium]_leptum_g__Oscillibacter
10BX37- s__uncultured_bacterium_g__norank_f__Muribaculaceae
10BX38- s__uncultured_bacterium_g__Prevotellaceae_UCG-001
10BX39- s__uncultured_bacterium_g__Lachnospiraceae_NK4A136_group
10BX40- s__unclassified_g__norank_f__Muribaculaceae
10BX41- s__Aerococcus_viridans
10BX42- s__Staphylococcus_lentus_g__Staphylococcus
10BX43- s__uncultured_organism_g__[Eubacterium]_ventriosum_group
10BX44- s__Corynebacterium_stationis
10BX45- s__uncultured_bacterium_g__Muribaculum
10BX46- s__uncultured_Bacteroidales_bacterium_g__norank_f__Muribaculaceae
10BX47- s__unclassified_g__Ruminococcus_1
10BX48- s__Bifidobacterium_pseudolongum_PV8-2
10BX49- s__uncultured_bacterium_g__Lachnoclostridium
10BX50- s__Lachnospiraceae_bacterium_DW12

FIG. 10B (con't)

10BY1- (3beta,17alpha,23R)-17,23-Epoxy-3,29-dihydroxy-27-norlanost-8-ene-15,24-dione
10BY2- metab_1110
10BY3- metab_2
10BY4- metab_3979
10BY5- metab_824
10BY6- metab_2781
10BY7- metab_943
10BY8- metab_796
10BY9- metab_960
10BY10- metab_3362
10BY11- Pregnan-20-one,17-(acetyloxy)-3-hydroxy-6-methyl-,(3b,5b,6a)-
10BY12- metab_664
10BY13- metab_3106
10BY14- metab_649
10BY15- metab_1
10BY16- metab_4150
10BY17- metab_487
10BY18- metab_469
10BY19- metab_5084
10BY20- metab_1364
10BY21- metab_4755
10BY22- metab_5022
10BY23- metab_1320
10BY24- metab_5050
10BY25- metab_1386
10BY26- metab_5274
10BY27- metab_288
10BY28- metab_4955
10BY29- metab_1419
10BY30- metab_1321
10BY31- metab_1704
10BY32- metab_4996
10BY33- metab_436
10BY34- metab_1632
10BY35- metab_5082
10BY36- metab_1350
10BY37- metab_458
10BY38- metab_1740
10BY39- metab_1421
10BY40- metab_859
10BY41- metab_434
10BY42- metab_472
10BY43- metab_53
10BY44- metab_213
10BY45- metab_218
10BY46- metab_211
10BY47- metab_417
10BY48- PG(18:1(9Z)/0:0)
10BY49- metab_56
10BY50- metab_3343

FIG. 10B (con't)

10CX1- s__uncultured_bacterium_g__Muribaculum
10CX2- s__Aerococcus_viridans
10CX3- s__Staphylococcus_cohnii_g__Staphylococcus
10CX4- s__uncultured_bacterium_g__Lachnospiraceae_NK4A136_group
10CX5- s__Bifidobacterium_pseudolongum_PV8-2
10CX6- s__uncultured_Bacteroidales_bacterium_g__norank_f__Muribaculaceae
10CX7- s__unclassified_g__Ruminococcus_1
10CX8- s__uncultured_bacterium_g__norank_f__Muribaculaceae
10CX9- s__unclassified_o__Bacteroidales
10CX10- s__unclassified_g__norank_f__Muribaculaceae
10CX11- s__uncultured_bacterium_g__Prevotellaceae_UCG-001
10CX12- s__uncultured_bacterium_g__Ruminococcaceae_UCG-014
10CX13- s__uncultured_bacterium_g__norank_f__Lachnospiraceae
10CX14- s__unclassified_g__Ruminiclostridium_9
10CX15- s__[Clostridium]_leptum_g__Oscillibacter
10CX16- s__uncultured_organism_g__[Eubacterium]_ventriosum_group
10CX17- s__uncultured_bacterium_g__Alistipes
10CX18- s__unclassified_g__Rikenellaceae_RC9_gut_group
10CX19- s__uncultured_Bacteroidales_bacterium_g__Alloprevotella
10CX20- s__Bacteroides_caecimuris
10CX21- s__uncultured_organism_g__Parabacteroides
10CX22- s__Bacteroides_acidifaciens
10CX23- s__unclassified_g__Helicobacter
10CX24- s__Staphylococcus_lentus_g__Staphylococcus
10CX25- s__Myroides_odoratimimus
10CX26- s__Corynebacterium_stationis
10CX27- s__Corynebacterium_glutamicum
10CX28- s__uncultured_bacterium_g__[Eubacterium]_xylanophilum_group
10CX29- s__unclassified_g__Bacteroides
10CX30- s__unclassified_g__Psychrobacter
10CX31- s__unclassified_g__Lactobacillus
10CX32- s__Lactobacillus_reuteri
10CX33- s__unclassified_g__Ruminococcaceae_UCG-014
10CX34- s__unclassified_f__Ruminococcaceae
10CX35- s__uncultured_bacterium_g__Ruminiclostridium_5
10CX36- s__unclassified_g__norank_f__Peptococcaceae
10CX37- s__unclassified_f__Lachnospiraceae
10CX38- s__uncultured_bacterium_g__Candidatus_Saccharimonas
10CX39- s__unclassified_g__norank_f__Ruminococcaceae
10CX40- s__unclassified_g__Roseburia
10CX41- s__Bacteroides_sartorii
10CX42- s__unclassified_g__Parabacteroides
10CX43- s__uncultured_Clostridiales_bacterium_g__Lachnospiraceae_NK4A136_group
10CX44- s__uncultured_bacterium_g__Lachnoclostridium
10CX45- s__Lachnospiraceae_bacterium_A4
10CX46- s__unclassified_g__norank_f__Lachnospiraceae
10CX47- s__unclassified_g__Lachnospiraceae_NK4A136_group
10CX48- s__uncultured_bacterium_g__norank_f__Desulfovibrionaceae
10CX49- s__uncultured_bacterium_g__Ruminiclostridium
10CX50- s__unclassified_g__Akkermansia

FIG. 10C (con't)

10CY1- PC(16:0/0:0)[U]
10CY2- metab_176
10CY3- 1alpha,24-Dihydroxy-22-ene-24-cyclopropylvitamin D3
10CY4- metab_1407
10CY5- metab_5503
10CY6- metab_3321
10CY7- metab_1427
10CY8- metab_1409
10CY9- metab_836
10CY10- metab_3322
10CY11- metab_947
10CY12- metab_987
10CY13- metab_1108
10CY14- metab_299
10CY15- metab_5585
10CY16- (3beta,17alpha,23R)-17,23-Epoxy-3,29-dihydroxy-27-norlanost-8-ene-15,24-dione
10CY17- metab_58
10CY18- metab_3708
10CY19- (22S)-1alpha,22,25-trihydroxy-26,27-dimethyl-23,23,24,24-tetradehydrovitamin D3
10CY20- metab_1189
10CY21- metab_935
10CY22- metab_664
10CY23- Pregnan-20-one,17-(acetyloxy)-3-hydroxy-6-methyl-,(3b,5b,6a)-
10CY24- metab_662
10CY25- metab_1182
10CY26- Pantothenic Acid
10CY27- metab_42
10CY28- L-Methionine
10CY29- Riboflavin (Vitamin B2)
10CY30- 9R,10S-epoxy-stearic acid
10CY31- metab_401
10CY32- metab_218
10CY33- metab_211
10CY34- metab_219
10CY35- metab_3343
10CY36- PG(16:0/0:0)[U]
10CY37- metab_3361
10CY38- metab_56
10CY39- metab_3331
10CY40- metab_1414
10CY41- metab_161
10CY42- metab_2900
10CY43- metab_2854
10CY44- metab_592
10CY45- metab_160
10CY46- Niacin (Nicotinic acid)
10CY47- metab_213
10CY48- PG(18:1(9Z)/0:0)
10CY49- metab_1059
10CY50- metab_2608

FIG. 10C (con't)

11Y1- Lactobacillus
11Y2- Ruminococcaceae_UCG-014
11Y3- Lachnoclostridium
11Y4- Akkermansia
11Y5- Bifidobacterium
11Y6- Faecalibaculum
11Y7- [Eubacterium]_ventriosum_group
11Y8- Helicobacter
11Y9- Prevotellaceae_UCG-001
11Y10- unclassified_o_Bacteroidales
11Y11- Bacteroides
11Y12- Alloprevotella
11Y13- Myroides
11Y14- Psychrobacter
11Y15- Staphylococcus
11Y16- Corynebacyerium_1
11Y17- Aerococcus
11Y18- Marvinbryantia
11Y19- [Eubacterium]_xylanophilum_group
11Y20- A2
11Y21- Ruminococcus_1
11Y22- norank_f_Muribaculaceae
11Y23- Muribaculum
11Y24- Ruminococcaceae_UCG-013
11Y25- norank_f_Desulfovibrionaceae
11Y26- Ruminiclostridium
11Y27- Anaerotruncus
11Y28- Mucispirillum
11Y29- Parabacteroides
11Y30- Alistipes
11Y31- norank_f_Erysipelotrichaceae
11Y32- Rikenellaceae_RC9_gut_group
11Y33- Candidatus_Saccharimonas
11Y34- norank_f_Peptococcaceae
11Y35- Ruminiclostridium_9
11Y36- norank_f_norank_o_Mollicutes_RF39
11Y37- Oscillibacter
11Y38- norank_f_Lachnospiraceae
11Y39- Roseburia
11Y40- unclassified_f_Lachnospiraceae
11Y41- norank_f_Ruminococcaceae
11Y42- Ruminiclostridium_5
11Y43- Lachnospiraceae_NK4A136_group
11Y44- Lachnospiraceae_UCG-006
11Y45- Enterorhabdus
11Y46- Blautia
11Y47- Parasutterella
11Y48- unclassified_f_Ruminococcaceae
11Y49- norank_f_Clostridiales_vadinBB60_group

FIG. 11 (con't)

12AY1- Ganosporelactone A
12AY2- Sophoraflavanone B
12AY3- Adhumulone
12AY4- Hydrocortamate
12AY5- 2-Deoxygalactopyranose
12AY6- PC(16:0/0:0)[U]
12AY7- Pregnan-20-one, 17-(acetyloxy)-3-hydroxy-6-methyl-, (3b,5b,6a)-
12AY8- 24S-OH-7-DHC
12AY9- 7-dehydrocholesterol
12AY10- 3a,7a,12b-Trihydroxy-5b-cholanoic acid
12AY11- A-L-Arabinofuranosyl-(1->2)-[a-D-mannopyranosyl-(1->6)]-D-mannose
12AY12- Vinaginsenoside R14
12AY13- Acetoxy-8-gingerol
12AY14- LysoPE(16:1(9Z)/0:0)
12AY15- 3-Hydroxy-4,6-heptadiyne-1-yl 1-glucoside
12AY16- (20S)-1alpha,20,25-trihydroxy-26,27-dimethyl-24a-homovitamin D3
12AY17- (±)13-HpODE
12AY18- 7S,8S-DiHOTrE
12AY19- Kynurenic acid
12AY20- Alpha-(Methylenecyclopropyl)glycine
12AY21- Glycyl-Phenylalanine
12AY22- Diosmin
12AY23- N-Acetylgalactosamine
12AY24- PG(18:1(9Z)/0:0)
12AY25- 9,10-epoxy-12-octadecenoic acid
12AY26- Sorbitan laurate
12AY27- Linoelaidic Acid
12AY28- (±)9-HpODE
12AY29- (±)12,13-DiHOME
12AY30- 23-Acetoxysoladulcidine
12AY31- PG(16:0/0:0)[U]
12AY32- Ciclesonide
12AY33- Momordol
12AY34- Floionolic acid
12AY35- Gamma-Tocotrienol
12AY36- Phaseolic acid
12AY37- Homoveratric acid
12AY38- (1S,2S,4S,5R)-1,8-Epoxy-p-menthane-2,5-diol
12AY39- 4-ene-Valproic acid
12AY40- 3-Hydroxydodecanedioic acid
12AY41- 13(S)-HpOTrE
12AY42- Deoxypyridinoline
12AY43- 4-Hydroxyproline galactoside
12AY44- 19-Norandrosterone
12AY45- 5-cis Carbaprostacyclin
12AY46- Ricinoleic Acid methyl ester
12AY47- Pantothenic Acid
12AY48- Thymine
12AY49- Spirolide E
12AY50- L-a-Lysophosphatidylserine

FIG. 12A (con't)

12BY1- metab_960
12BY2- metab_796
12BY3- metab_943
12BY4- metab_2781
12BY5- metab_3106
12BY6- metab_3362
12BY7- metab_824
12BY8- metab_664
12BY9- (3beta,17alpha,23R)-17,23-Epoxy-3,29-dihydroxy-27-norlanost-8-ene-15,24-dione
12BY10- metab_1110
12BY11- metab_2
12BY12- metab_3979
12BY13- Pregnan-20-one, 17-(acetyloxy)-3-hydroxy-6-methyl-, (3b,5b,6a)-
12BY14- metab_649
12BY15- metab_1
12BY16- metab_4150
12BY17- PG(18:1(9Z)/0:0)
12BY18- metab_3343
12BY19- metab_56
12BY20- metab_469
12BY21- metab_1364
12BY22- metab_487
12BY23- metab_5084
12BY24- metab_859
12BY25- metab_472
12BY26- metab_213
12BY27- metab_218
12BY28- metab_211
12BY29- metab_417
12BY30- metab_434
12BY31- metab_53
12BY32- metab_1320
12BY33- metab_4755
12BY34- metab_5022
12BY35- metab_288
12BY36- metab_1704
12BY37- metab_5050
12BY38- metab_1386
12BY39- metab_4955
12BY40- metab_1321
12BY41- metab_1419
12BY42- metab_4996
12BY43- metab_5082
12BY44- metab_1350
12BY45- metab_1740
12BY46- metab_1421
12BY47- metab_5274
12BY48- metab_436
12BY49- metab_1632
12BY50- metab_458

FIG. 12B(con't)

12CY1- metab_176
12CY2- 1alpha,24-Dihydroxy-22-ene-24-cyclopropylvitamin D3
12CY3- metab_3322
12CY4- metab_836
12CY5- metab_947
12CY6- metab_3708
12CY7- metab_2839
12CY8- PC(16:0/0:0)[U]
12CY9- metab_3321
12CY10- metab_592
12CY11- metab_935
12CY12- metab_987
12CY13- metab_1407
12CY14- metab_1427
12CY15- metab_1409
12CY16- Pregnan-20-one, 17-(acetyloxy)-3-hydroxy-6-methyl-, (3b,5b,6a)-
12CY17- metab_664
12CY18- metab_299
12CY19- metab_662
12CY20- metab_5585
12CY21- metab_1108
12CY22- metab_58
12CY23- (3beta,17alpha,23R)-17,23-Epoxy-3,29-dihydroxy-27-norlanost-8-ene-15,24-dione
12CY24- (22S)-1alpha,22,25-trihydroxy-26,27-dimethyl-23,23,24,24-tetradehydrovitamin D3
12CY25- metab_1189
12CY26- metab_2608
12CY27- metab_1059
12CY28- metab_160
12CY29- Niacin (Nicotinic acid)
12CY30- metab_3248
12CY31- metab_56
12CY32- metab_161
12CY33- metab_219
12CY34- metab_211
12CY35- metab_218
12CY36- metab_2900
12CY37- Riboflavin (Vitamin B2)
12CY38- 9R,10S-epoxy-stearic acid
12CY39- metab_3361
12CY40- metab_3331
12CY41- metab_2854
12CY42- L-Methionine
12CY43- PG(18:1(9Z)/0:0)
12CY44- metab_401
12CY45- metab_3343
12CY46- PG(16:0/0:0)[U]
12CY47- metab_42
12CY48- metab_1182
12CY49- metab_213
12CY50- Pantothenic Acid

FIG. 12C(con't)

USE OF PAYCS IN REGULATION OF INTESTINAL FLORA, METABOLITES, AND BRAIN NEUROTRANSMITTERS

CROSS-REFERENCE TO RELATED APPLICATION

This patent application claims the benefit and priority of Chinese Patent Application No. 202210147703.1 filed with the China National Intellectual Property Administration on Feb. 17, 2022, the disclosure of which is incorporated by reference herein in its entirety as part of the present application.

REFERENCE TO SEQUENCE LISTING

The present application is being filed along with a Sequence Listing in electronic format. The Sequence Listing is provided as a file entitled "2023-06-15 Sequence Listing-BGI018-001AUS.xml" created on Jun. 15, 2023, which is about 2,308 bytes in size. The information in the electronic format of the Sequence Listing is incorporated herein by reference in its entirety.

TECHNICAL FIELD

The present disclosure belongs to the technical field of health food, and in particular, relates to the use of PAYCS (the peptide Pro-Ala-Tyr-Cys-Ser, SEQ ID NO: 1) in the regulation of intestinal flora, metabolites, and brain neurotransmitters.

BACKGROUND

At present, the brain-gut axis is a bilateral/bi-directional information exchange system that integrates brain and intestinal functions, and the two-way interaction between the central nervous system, enteric nervous system, and gastrointestinal tract is also receiving increasing attention. Intestinal microorganisms participate in the functional response of the brain-gut axis and play a very important role in the exchange of information between the gut and the brain, thus medical scientists proposed a concept of the "microbiota-gut-brain axis". Changes in the function of brain-gut axis would cause a variety of gastrointestinal tract diseases such as irritable bowel syndrome and related functional gastrointestinal tract diseases. Recent studies have also found that dysfunction of the brain-gut axis is also responsible for the development of many brain diseases, including autism, Parkinson's disease, mood and emotion disorders, and chronic pains.

Generally speaking, aging, menopause, Alzheimer's disease, brain ischemia, etc. will cause the body, especially the brain, to decline in function and memory. It is believed in modern medicine that this is associated with the decline in the function of hippocampus of the brain, and scopolamine is often used in medical trials to block its neural pathways. Studies on the regulation of the axis of intestinal microorganism-metabolism-neurotransmitter have not been reported.

Through the above analysis, the problems and defects of the prior arts lie in that studies on bioactive peptides that are capable of improving scopolamine-induced memory defects by improving the pathway of tryptophan neurotransmitter have not been reported in prior arts.

The difficulty of solving the above problem and defects is due to the complexity of Alzheimer's disease in which memory decline is caused by many factors. Most nutritional supplements are studied as antioxidants, but the relationship between memory decline and intestinal flora, metabolism, and neurotransmitter. In those studies, most plant extracts had desirable effects in memory improvement, but the processes for the preparation of the plant extracts were complicated, and the introduction of organic reagents was costly.

The significance of solving the above problems and defects is that the neuroprotective peptide PAYCS (SEQ ID NO: 1) is obtained through targeted isolation from anchovies. The preparation process is a green and simple one. By practicing the embodiments of the present disclosure, the improvement effect of the bioactive polypeptide on memory impairment through the regulation of intestinal flora, intestinal metabolism and brain neurotransmitters can be identified.

SUMMARY

In view of the problems existing in the prior arts, the present disclosure provides the use of PAYCS (SEQ ID NO: 1) in regulating intestinal flora, metabolites, and brain neurotransmitters.

The present disclosure is achieved by implementing the following technical proposal. Provided is the use of PAYCS (SEQ ID NO: 1) in regulation of intestinal flora, metabolites, and brain neurotransmitters, comprising: remedying scopolamine-induced memory impairment in mice through targeted oxidation, inflammatory stress, and regulation of the intestinal microorganism-metabolite-brain neurotransmitter axis by PAYCS (SEQ ID NO: 1).

PAYCS (SEQ ID NO: 1) may be prepared by using a process including the following conditions for enzymatic hydrolysis by protease:material-liquid ratio 1:3, enzyme dosage 1.3% by weight of the material, pH 7.2, reaction temperature 60° C., and reaction time 50 min. The conditions for enzymatic hydrolysis using an alkaline protease are: an enzyme dosage of 0.32%, a pH value of 7.3, a reaction temperature: 63° C., and a reaction time of 77 min.

In a further embodiment of the present disclosure, the alkaline protease is subjected to a second enzymatic hydrolysis. After the second enzymatic hydrolysis is completed, a heater temperature is adjusted, the pH of the resulting material is adjusted to the desired value using HCl, and glucoamylase is added to degrade the polysaccharide.

Upon completion of inactivation of the enzyme, the resulting materials are fully inactivated at 96° C., and the heater, the homogenization pump, and the valves are closed, and a cooling water circulating pump is started to promote cooling of the materials. When the temperature drops to 43° C., all the pumps and the valves are closed, the discharge valve is opened, and enzymatic hydrolysate is stored in a barrel.

In a further embodiment of the present disclosure, a decolorization step is conducted as follows: the enzymatic hydrolysate is centrifuged at 4,100×rpm for 22 min and the enzymatic hydrolysate is filtered using an 11-kDa ultrafiltration membrane. The supernatant is decolonized with an ultrafiltration membrane, with an inlet pressure of 0.09 MPa, an outlet pressure of 0.07 MPa, and a material temperature of 26° C. During the whole process, circulating cooling water is used to prevent temperature rise in the material, and a membrane throughput is determined by calculating the volume of outflow liquid within the measurement time.

In a further embodiment of the present disclosure, the method comprises cleaning the membrane using a forward cleaning process. Firstly, residues in the membrane system are removed with clean water, and a membrane cleaning agent is added to perform circulated cleaning for 61 min. The cleaning solution is removed, and then the membrane system is washed with clean water until the eluate becomes clear, contains no foams and the pH value becomes neutral. Then a reverse cleaning process is performed as follows: residues in the membrane system are removed with clean water, the ultrafiltration membrane is disassembled and placed and assembled in a direction opposite to the initial direction, and then the ultrafiltration membrane is cleaned using a forward cleaning procedure.

After a spray dryer is cleaned, a dryer and a heater are turned on to dry the water inside the dryer. An atomizer and a feed pump are turned on and the material is sprayed. An inlet temperature is 150° C., a frequency of a nebulizer is set at 370 Hz, and a speed of a peristaltic pump is set at 18 rpm.

In a further embodiment of the present disclosure, PAYCS-L (lower dose of SEQ ID NO: 1) and PAYCS-H (higher dose of SEQ ID NO: 1) exhibit different memory mitigation effects in Alzheimer's disease (AD) model mice.

In a further embodiment of the present disclosure, PAYCS (SEQ ID NO: 1) has a positive effect on both liver and serum deficits.

In a further embodiment of the present disclosure, PAYCS-H (higher dose of SEQ ID NO: 1) has good anti-oxidant and anti-inflammatory effects.

In a further embodiment of the present disclosure, PAYCS-L (lower dose of SEQ ID NO: 1) reconstitutes the abundance of intestinal microorganism population in amnesic mice.

In a further embodiment of the present disclosure, PAYCS (SEQ ID NO: 1) has a regulatory effect on brain neurotransmitters and fecal metabolites in amnesic mice.

Through combining all technical solutions as described above, the present disclosure provides the following advantages and positive effects: PAYCS (SEQ ID NO: 1) provided by the present disclosure is used to regulate intestinal flora, metabolites, and brain neurotransmitters. Through targeted oxidation, inflammatory stress, and regulation of the intestinal microorganism-metabolite-brain neurotransmitter axis, PAYCS (SEQ ID NO: 1) remedies scopolamine-induced memory impairment in mice.

The bioactive peptide PAYCS (Pro-Ala-Tyr-Cys-Ser) (SEQ ID NO: 1) derived from anchovy hydrolysate has shown an effect of memory improvement. The intestinal microbiota-brain axis plays an important role in brain functions which may be affected by nutritional supplements. In the scopolamine-induced mouse model, a better effect of memory enhancement was shown in the training part of the behavioral test following 3 weeks of treatment with PAYCS-L (0.2 g/kg bw, lower dose of SEQ ID NO: 1), while 3 weeks of treatment with PAYCS-H (0.4 g/kg bw, higher dose of SEQ ID NO: 1) showed better improvement in cognitive function in the test part. PAYCS (SEQ ID NO: 1) can significantly reduce the MDA and LDH levels in serum and significantly increase SOD content in the liver. PAYCS-H (higher dose of SEQ ID NO: 1) can inhibit the increase of both TNF-α and IL-1β in the liver, while PAYCS-L (lower dose of SEQ ID NO: 1) only reduces the content of TNF-α in the liver. The results of 16S rRNA analysis showed that PAYCS-L (lower dose of SEQ ID NO: 1) changed the ratio of Bacteroidetes/Firmicutes, and PAYCS (SEQ ID NO: 1) increased the relative abundance of plants such as Cacteroidaceae and Prevotellaceae. It is noted that memory-related metabolites (e.g., blumealactone C, thalictroidine, notoginsenoside M, 3a,7a,12b-trihydroxy-5b-cholanoic acid, sequiterpene lactone 326, helenalin, and cholic acid) and neurotransmitters (e.g., Ach, GABA, Glu, HisA, and Kyn) are significantly up-regulated. Therefore, different doses of PAYCS (SEQ ID NO: 1) exhibit memory-relieving effects through different pathways. PAYCS-L (lower dose of SEQ ID NO: 1) partially reverses memory deficits in amnesic mice by regulating the intestinal microorganism-metabolites-brain neurotransmitter axis. PAYCS-H (higher dose of SEQ ID NO: 1) reverses oxidative and inflammatory stress in the liver and serum, which may be a key pathway for improving memory. And PAYCS-H (higher dose of SEQ ID NO: 1) re-modulates intestinal microorganisms and fecal Metabolites. PAYCS (SEQ ID NO: 1) increases the relative abundance of microbita such as Cacteroidaceae and Prevotellaceae and improves the tryptophan metabolism-related neurotransmitters in the brain.

BRIEF DESCRIPTION OF THE DRAWINGS

To illustrate the technical solutions of embodiments of the present disclosure more clearly, a brief introduction will be made to the drawings required in the embodiments of the present disclosure. Apparently, the drawings described below are only provided for some embodiments of the present disclosure, those of ordinary skill in the art can further obtain other drawings according to these drawings without making creative efforts.

FIG. 1A-FIG. 1H show the effect of PAYCS-L (lower dose of SEQ ID NO: 1) and PAYCS-H (higher dose of SEQ ID NO: 1) on the behavior of amnesic mice with amnesia induced by scopolamine.

FIG. 1A shows the test results of the jumping test in an embodiment of the present disclosure.

FIG. 1B shows test results of the swimming speed test in an embodiment of the present disclosure.

FIG. 1C shows the test results of the swimming distance test in an embodiment of the present disclosure.

FIG. 1D shows the test results of the number of crossings on the target platform.

FIG. 1E shows test results of the number of crossings between the target quadrants.

FIG. 1F shows the test results of the escape latency and error times during the training.

FIG. 1G shows the test results of the measurement results of swimming distance, swimming speed, and the number of crossings between the target quadrants.

FIG. 1H shows the number of crossings and escape latency on the target platform.

FIG. 2A-FIG. 2D show the effect of PAYCS-L (lower dose of SEQ ID NO: 1) and PAYCS-H (higher dose of SEQ ID NO: 1) on the liver and serum oxidation indexes of amnesic mice induced by scopolamine.

FIG. 2A shows the measurement results of MDA in mouse liver and serum.

FIG. 2B shows the measurement results of LDH in mouse liver and serum.

FIG. 2C shows the measurement results of SOD in mouse liver and serum.

FIG. 2D shows the measurement results of GP(x) in mouse liver and serum.

FIG. 3A-FIG. 3B show the effect of PAYCS-L (lower dose of SEQ ID NO: 1) and PAYCS-H (higher dose of SEQ ID NO: 1) on the liver and serum inflammatory indexes of mice with amnesia induced by scopolamine.

FIG. 3A shows the measurement results of IL-1β content in mouse liver and serum.

FIG. 4A shows a Venn diagram of a diversity at the OTU level.

FIG. 4B shows a diagram of the Student's test of Chao indexes.

FIG. 4C shows a histogram of community differences at the phylum level.

FIG. 4D shows the analysis of microflora difference between the control and the model at the species level.

FIG. 4E shows the analysis of microflora difference between PYACS-L and the model at the species level.

FIG. 4F shows the analysis of microflora difference between PYCS-H and the model at the species level.

FIG. 5A shows a Venn diagram of different metabolites.

FIG. 5B shows a cluster heat map of the metabolites.

FIG. 5C shows the analysis of the metabolite difference between the control and the model.

FIG. 5D shows the analysis of the metabolite difference between the model and PAYCS-L (lower dose of SEQ ID NO: 1).

FIG. 5E shows the analysis of the metabolite difference between the model and PAYCS-H (higher dose of SEQ ID NO: 1).

Figure 13:
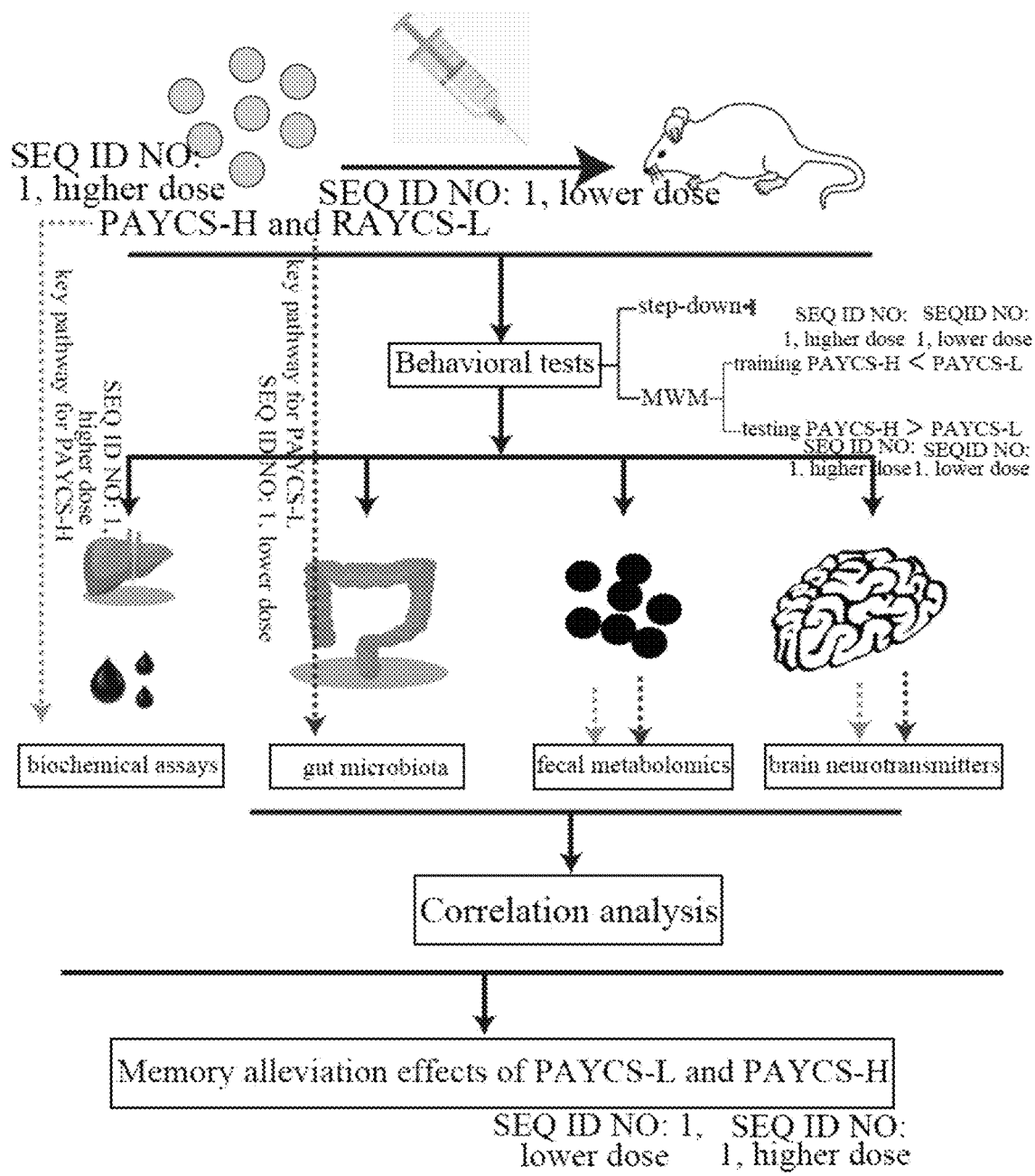

FIG. 13 schematic diagram of the mechanism of action of PAYCS (SEQ ID NO: 1) in remedying scopolamine-induced memory defects in mice.

DETAILED DESCRIPTION OF THE EMBODIMENTS

In order to make the objective, technical solutions, and advantages of the present disclosure clearer, the present disclosure is described below in more detail in conjunction with embodiments. It should be understood that the specific embodiments described herein are merely used to explain the present disclosure and are not intended to limit the present disclosure.

Given the problems existing in the prior arts, the present disclosure provides the use of PAYCS (SEQ ID NO: 1) in the regulation of intestinal flora, metabolites, and brain neurotransmitters, and the present disclosure will be described in detail below in conjunction with specific embodiments. PAYCS (SEQ ID NO: 1) is a polypeptide derived from the enzymatic hydrolysate of the fish of anchovies and supplementation of PAYCS (SEQ ID NO: 1) can regulate the intestinal flora-metabolite-brain neurotransmitter axis by improving serum, liver oxidation stress, and inflammatory injuries to improve efficacy in scopolamine-induced memory impairment in mice. PAYCS (SEQ ID NO: 1) can be used as medicine or a supplement. Supplementing PAYCS (SEQ ID NO: 1) allows for remedying scopolamine-induced memory impairment in mice through targeted oxidation, inflammatory stress, and regulation of the intestinal microorganism-metabolite-brain neurotransmitter axis.

PAYCS (SEQ ID NO: 1) may be prepared by using a process including the following conditions for enzymatic hydrolysis by protease:material-liquid ratio 1:3, enzyme dosage 1.3%, pH 7.2, reaction temperature 60° C., and reaction time 50 min. The conditions for enzymatic hydrolysis using an alkaline protease includes an enzyme dosage of 0.32%, a pH value of 7.3, a reaction temperature of 63° C., and a reaction time of 77 min.

In a further embodiment of the present disclosure, the alkaline protease is subject to a second enzymatic hydrolysis. After the second enzymatic hydrolysis is completed, a heater temperature is adjusted, the pH of the resulting material is adjusted to the desired value using HCl, and glucoamylase is added to degrade the polysaccharide.

Upon completion of inactivation of the enzyme, the resulting materials are fully inactivated at 96° C., and the heater, the homogenization pump, and the valves are closed, and a cooling water circulating pump is started to promote cooling of the materials. When the temperature drops to 43° C., all the pumps and the valves are closed, the discharge valve is opened, and enzymatic hydrolysate is stored in a barrel.

A decolorization step is conducted as follows: the enzymatic hydrolysate is centrifuged at 4,100× rpm for 22 min and filtering enzymatic hydrolysate using an 11-kDa ultrafiltration membrane. The supernatant is decolonized with an ultrafiltration membrane, with an inlet pressure of 0.09 MPa, an outlet pressure of 0.07 MPa, and a material temperature of 26° C. During the whole process, circulating cooling water is used to prevent temperature rise in the material, and a membrane throughput is determined by calculating the volume of outflow liquid within the measurement time.

The use comprises cleaning of the membrane using a forward cleaning process. Firstly, residues in the membrane system are removed with clean water, and a membrane cleaning agent is added to perform circulated cleaning for 61 min. The cleaning solution is removed, and then the membrane system is washed with clean water until the eluent becomes clear, contains no foams and the pH value becomes neutral. Then a reverse cleaning process is performed as follows: residues in the membrane system are removed with clean water, the ultrafiltration membrane is disassembled and placed and assembled in a direction opposite to the initial direction, and then the ultrafiltration membrane is cleaned using a forward cleaning procedure.

After a spray dryer is cleaned, a dryer and a heater are turned on to dry the water inside the dryer. An atomizer and a feed pump are turned on and the material is sprayed. An inlet temperature is 150° C., a frequency of a nebulizer is set at 370 Hz, and a speed of a peristaltic pump is set at 18 rpm.

As shown in FIG. 13, PAYCS (SEQ ID NO: 1) remedies scopolamine-induced memory impairment in mice through targeted oxidation, inflammatory stress, and regulation of the intestinal microorganism-metabolite-brain neurotransmitter axis.

The bioactive peptide PAYCS (Pro-Ala-Tyr-Cys-Ser) (SEQ ID NO: 1) extracted from anchovy hydrolysate has shown an effect of memory improvement. The intestinal microbiota-brain axis plays an important role in brain functions which may be affected by nutritional supplements. In the scopolamine-induced mouse model, a better effect of memory enhancement was shown in the training part of the behavioral test following 3 weeks of treatment with PAYCS-L (0.2 g/kg bw, lower dose of SEQ ID NO: 1), while 3 weeks of treatment with PAYCS-H (0.4 g/kg bw, higher dose of SEQ ID NO: 1) showed better improvement in cognitive function in the test part. PAYCS (SEQ ID NO: 1) can significantly reduce the MDA and LDH levels in serum and significantly increase SOD content in the liver. PAYCS-H (higher dose of SEQ ID NO: 1) can inhibit the increase of both TNF-α and IL-1β in the liver, while PAYCS-L (lower dose of SEQ ID NO: 1) only reduces the content of TNF-α in the liver. The results of 16S rRNA analysis showed that PAYCS-L (lower dose of SEQ ID NO: 1) changed the ratio of Bacteroides/Firmicutes, and PAYCS (SEQ ID NO: 1) increased the relative abundance of plants such as Cacteroidaceae and Prevotellaceae. It is noted that memory-related metabolites (e.g., Panax notoginseng saponins and cholinergic acid) and neurotransmitters (e.g., Ach, GABA, Glu, HisA, and Kyn) are significantly up-regulated. Therefore, different doses of PAYCS (SEQ ID NO: 1) exhibit memory-relieving effects through different pathways. PAYCS-L (lower dose of SEQ ID NO: 1) partially reverses memory deficits in amnesic mice by regulating the intestinal microorganism-metabolite-brain neurotransmitter axis. PAYCS-H (higher dose of SEQ ID NO: 1) reverses oxidative and inflammatory stress in the liver and serum, which may be a key pathway for improving memory. And PAYCS-H (higher dose of SEQ ID NO: 1) re-modulates intestinal microorganisms and fecal Metabolites.

The present disclosure is described in detail below in conjunction with the accompanying drawings.

FIG. 1 shows the effect of PAYCS-L (lower dose of SEQ ID NO: 1) and PAYCS-H (higher dose of SEQ ID NO: 1) on the behavior of mice with amnesia induced by scopolamine. The mice were tested for a jumping test (FIG. 1A), swimming speed (FIG. 1), swimming distance (FIG. 1C), the number of crossings on the target platform (FIG. 1D), the number of crossings on the target quadrants (FIG. 1E), the escape latency and the error times (FIG. 1F) during the training. In the test part, the swimming distance, the swimming speed, number of crossings on target quadrant (FIG. 1G), the number of crossings on the target platform, and escape latency (H) were determined. In these figures, #: compared with the control group, P<0.05; compared with the control group, P<0.01; *: compared model group, P<0.05; **: compared with the model group, P<0.01.

FIG. 2 shows the effects of PAYCS-L (lower dose of SEQ ID NO: 1) and PAYCS-H (higher dose of SEQ ID NO: 1) on liver and serum oxidation indexes of mice with amnesia induced by scopolamine and levels of MDA (FIG. 2A), LDH (FIG. 2B), SOD (FIG. 2C), and GP(x) (FIG. 2D) in the liver and the serum of mice were determined. #: compared with the control group, P<0.05; *: compared to the model group, P<0.05.

Figure 1A:
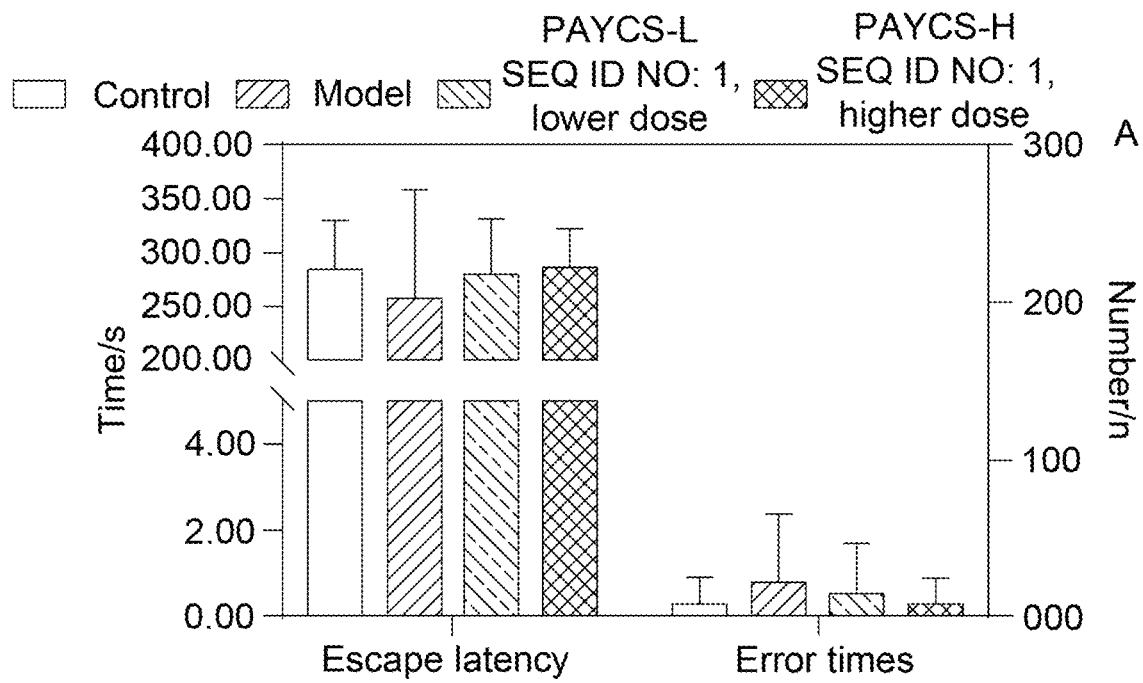
Figure 1B:
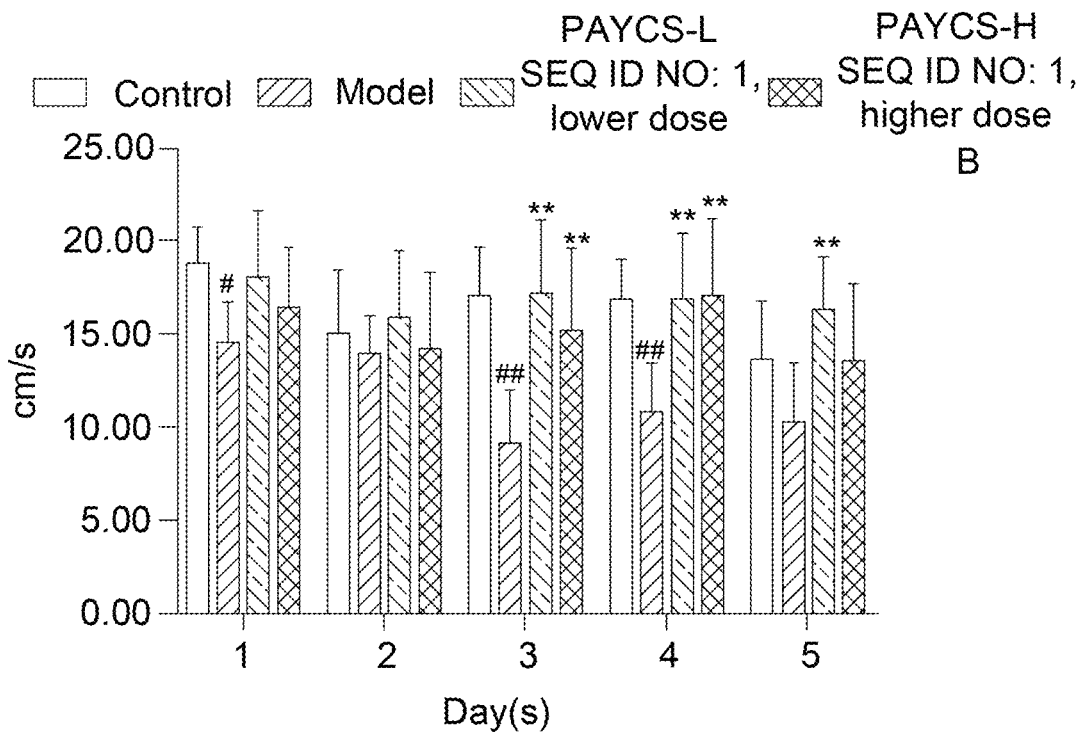
Figure 1C:
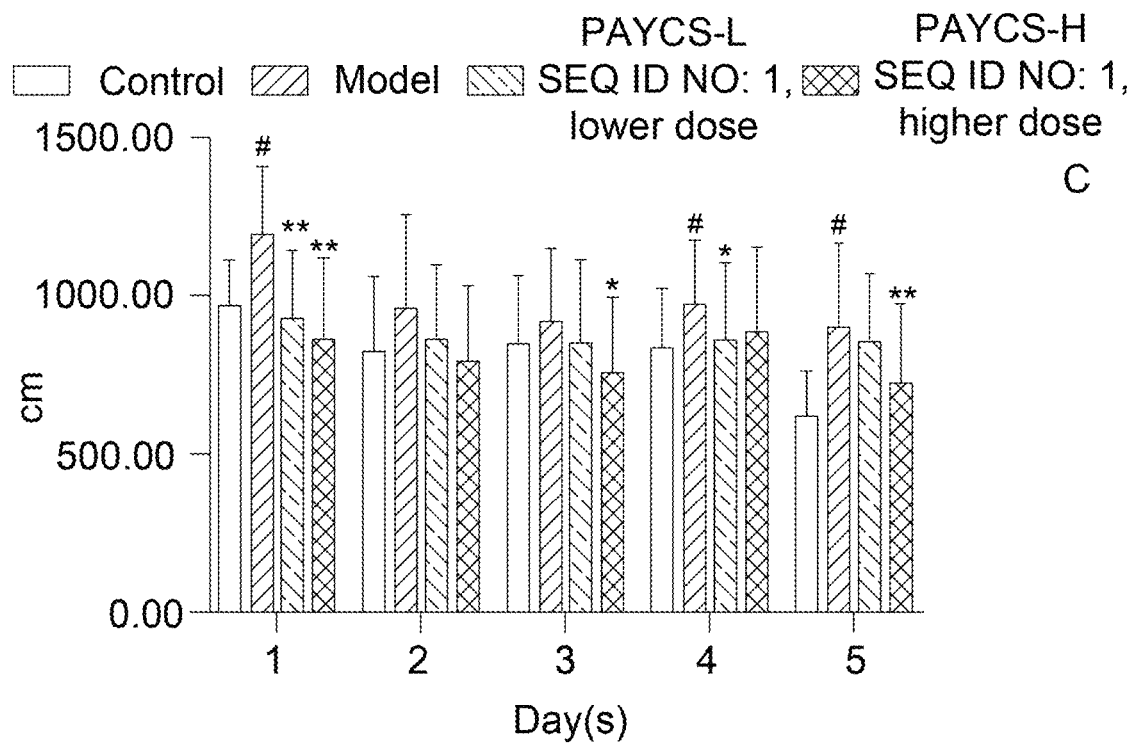
Figure 1D:
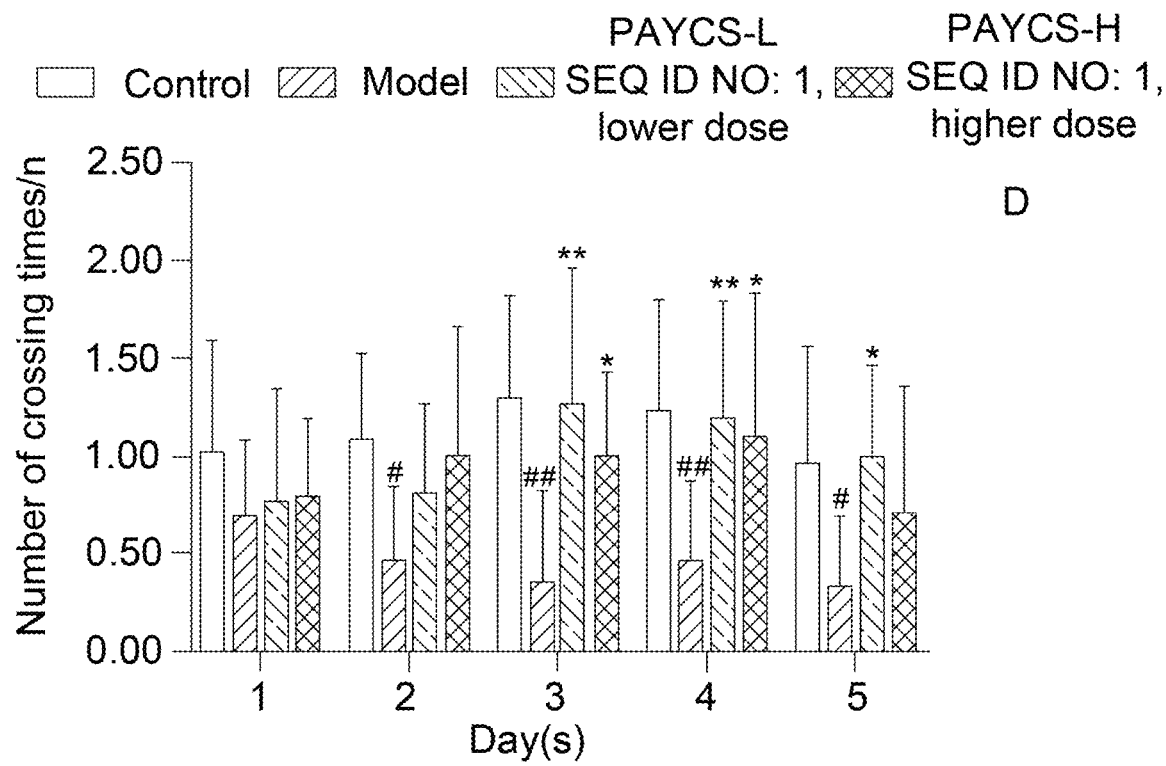
Figure 1E:
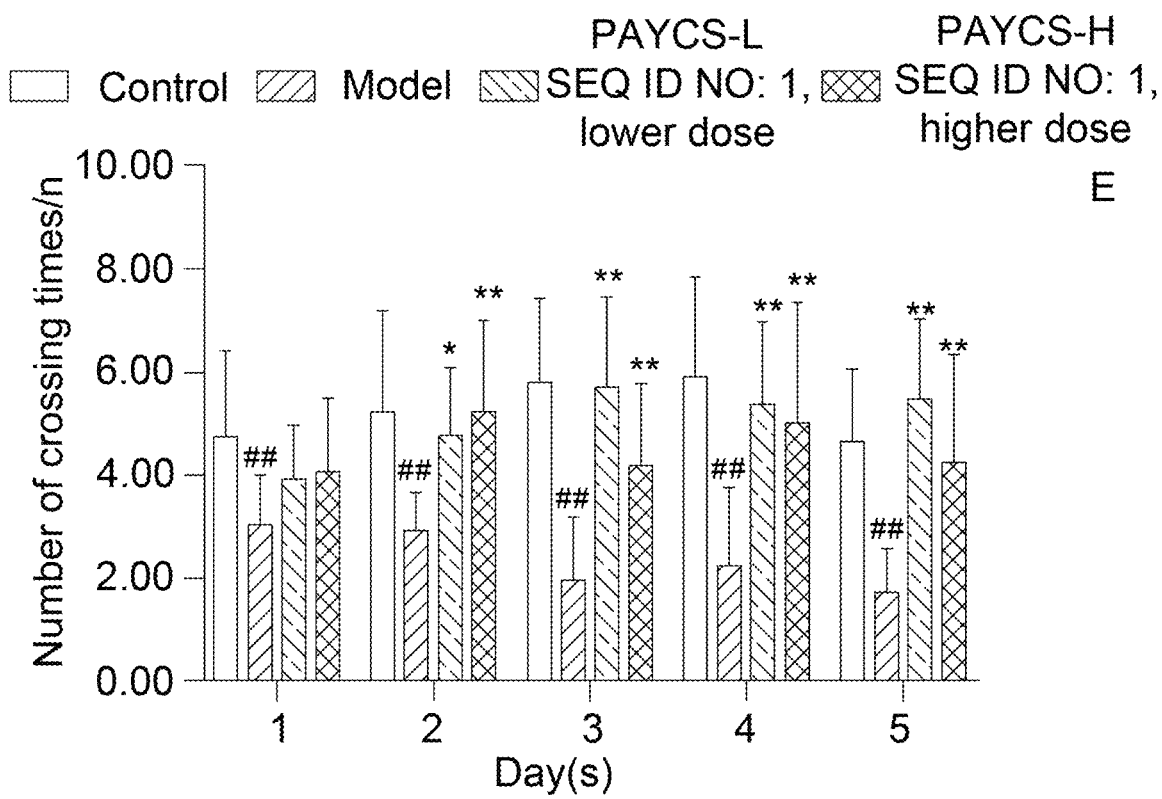
Figure 1F:
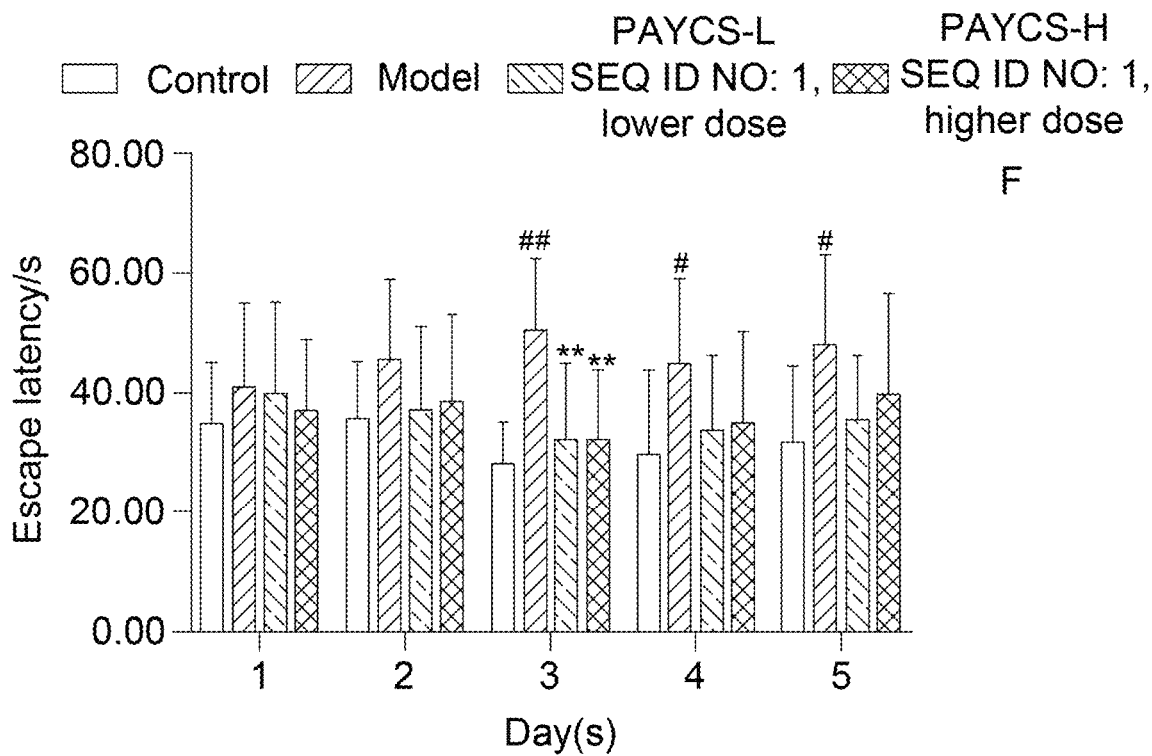
Figure 1G:
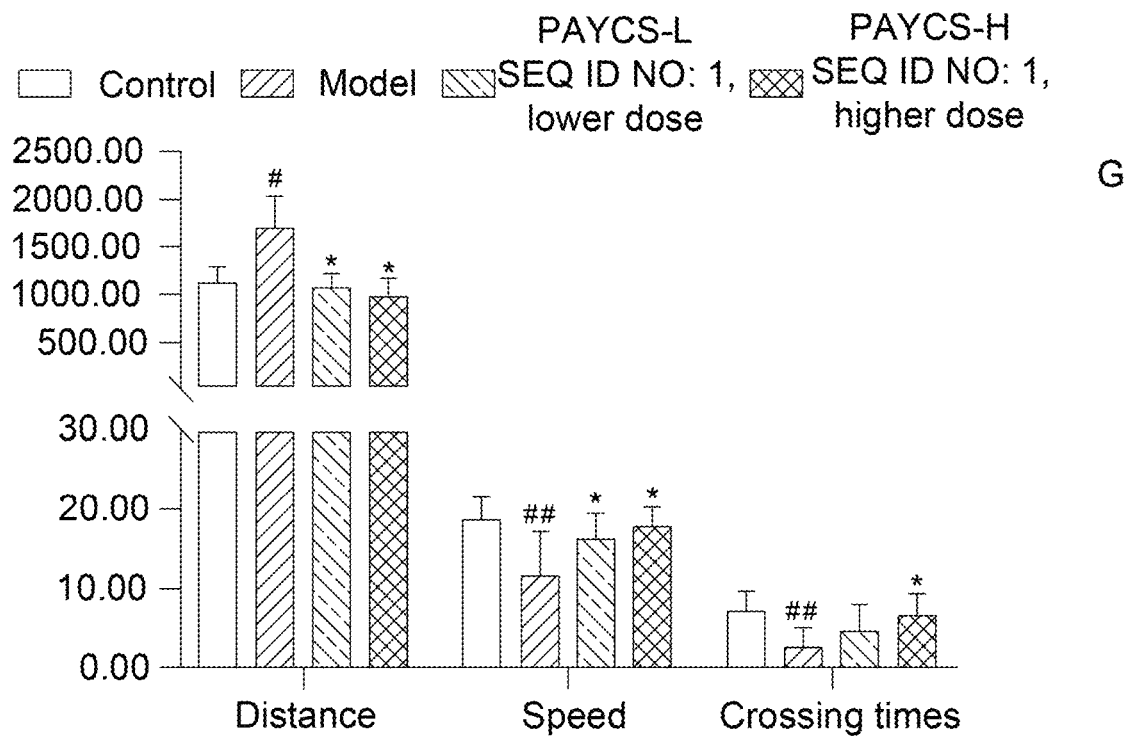
Figure 1H:
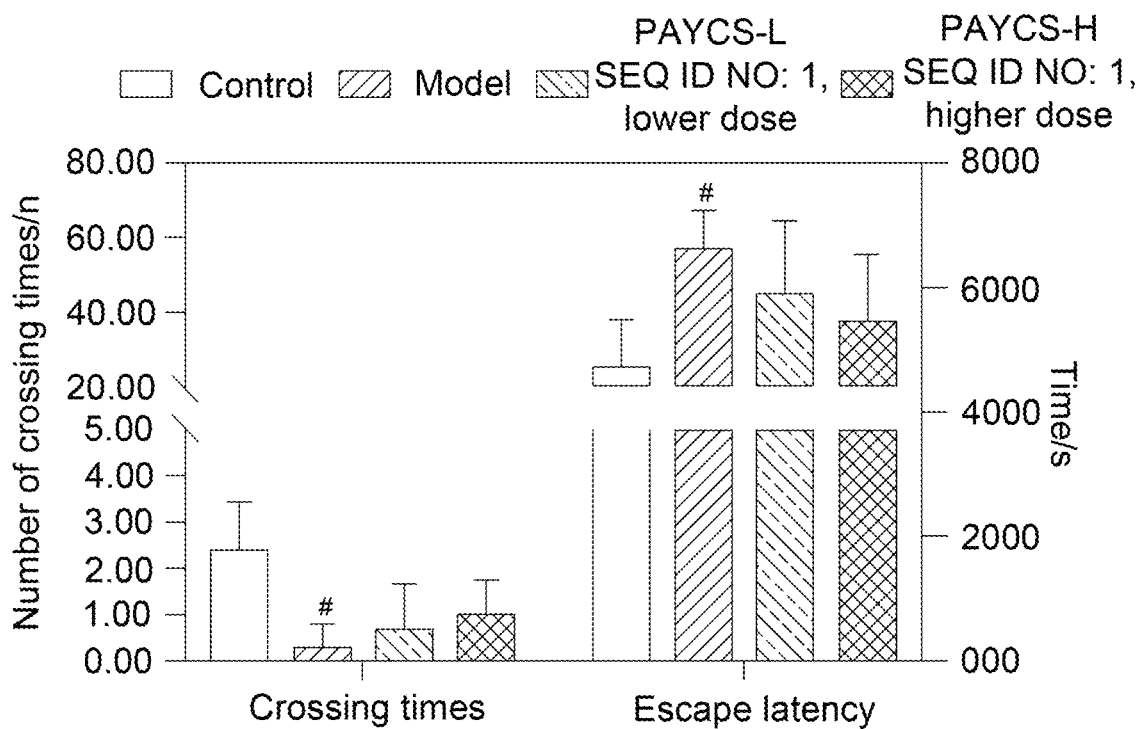
Figure 2A:
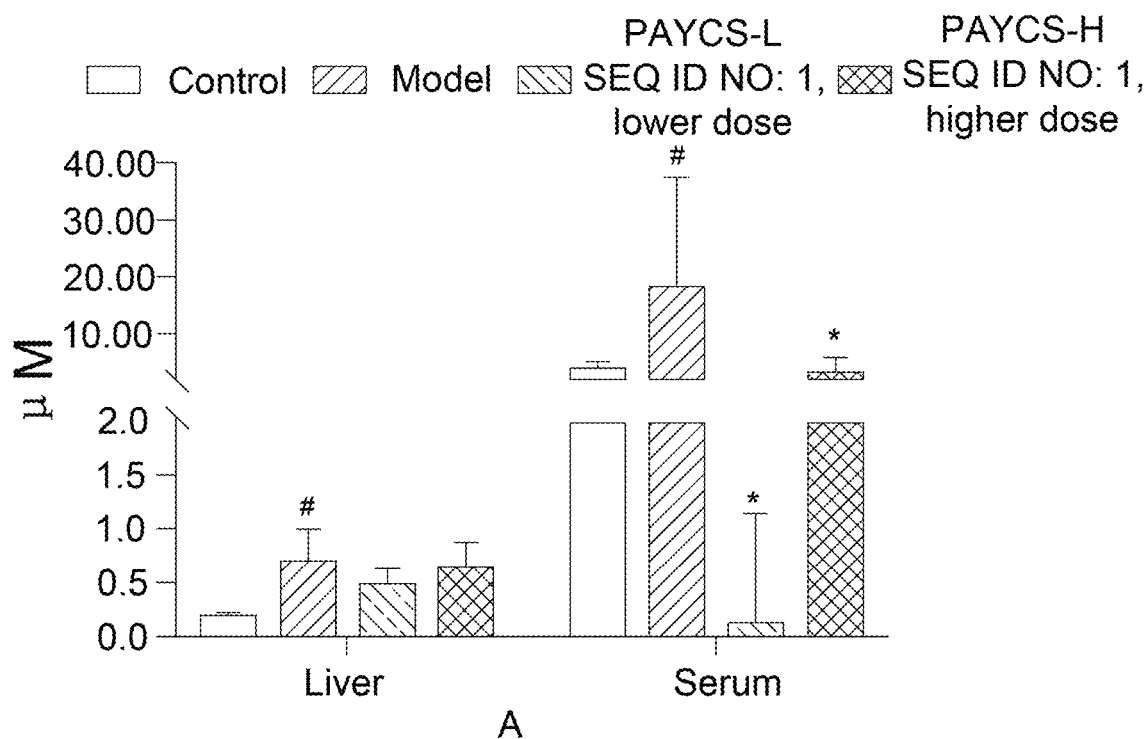
Figure 2B:
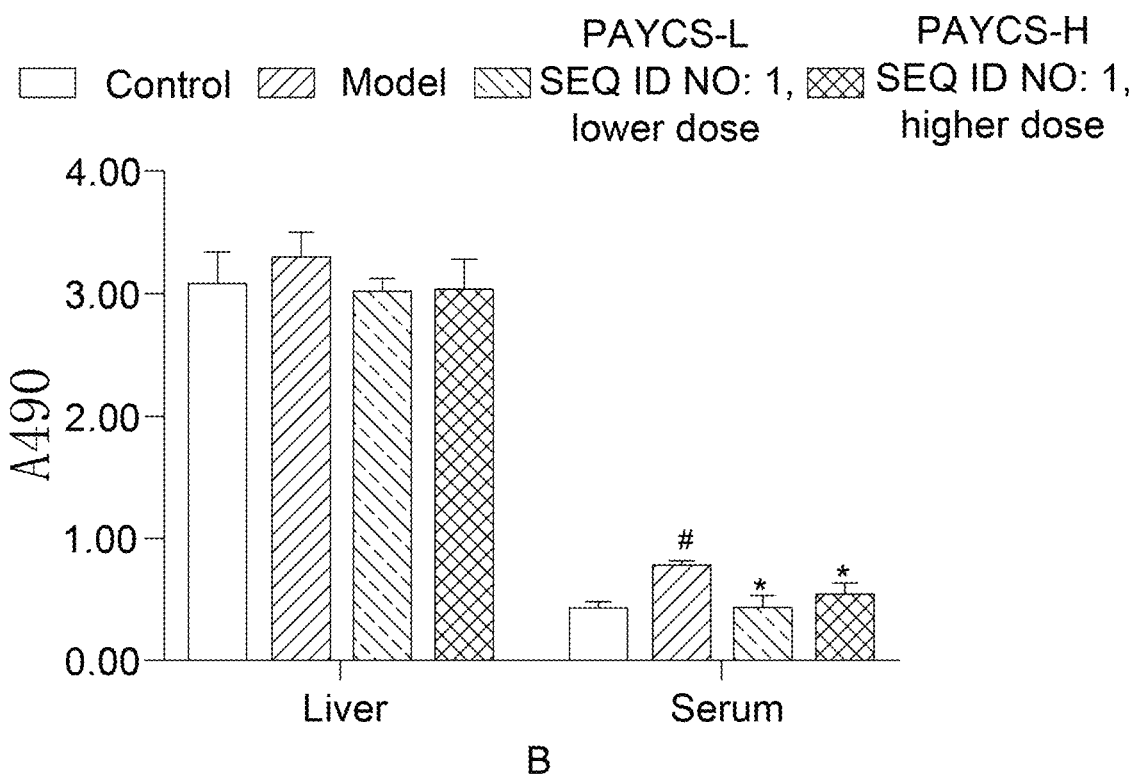
Figure 2C:
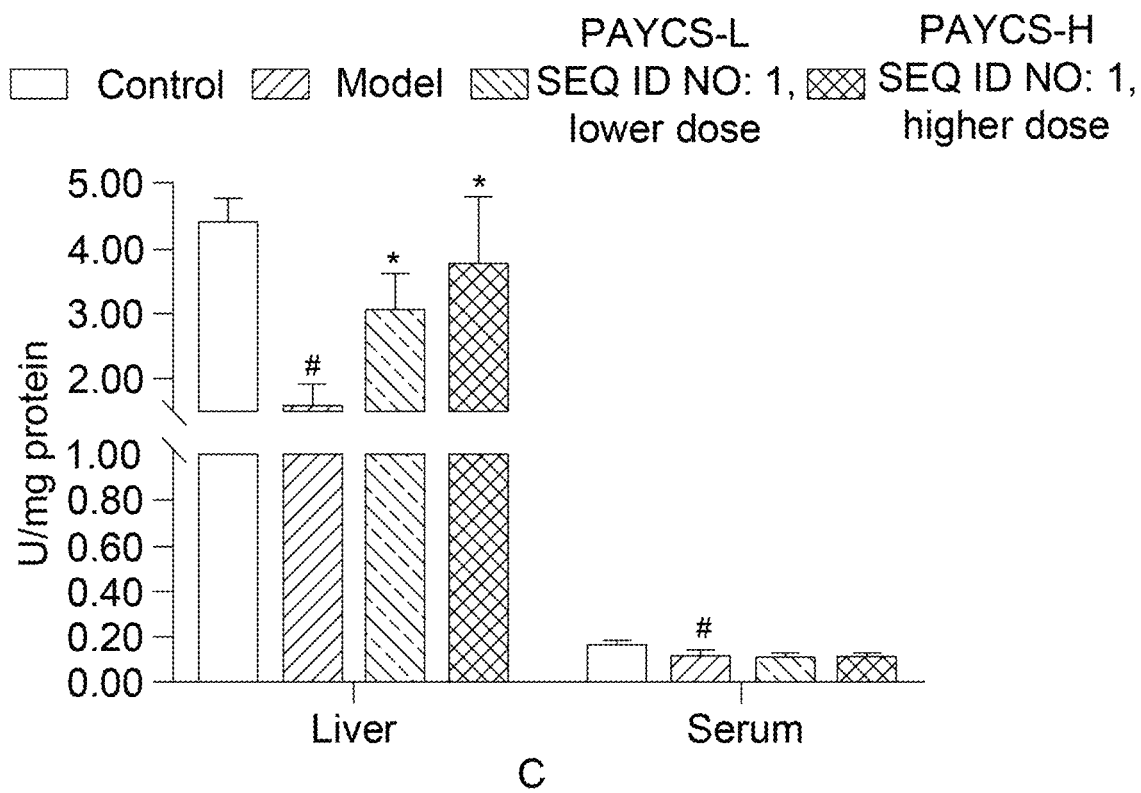
Figure 2D:
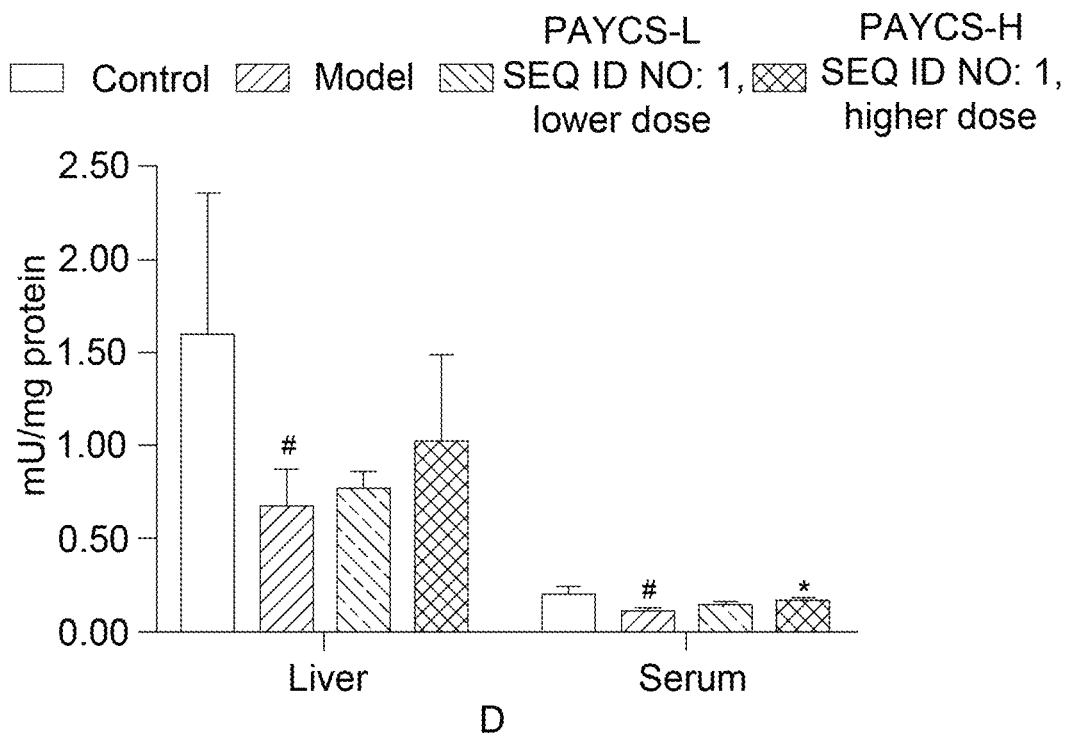
Figure 3A:
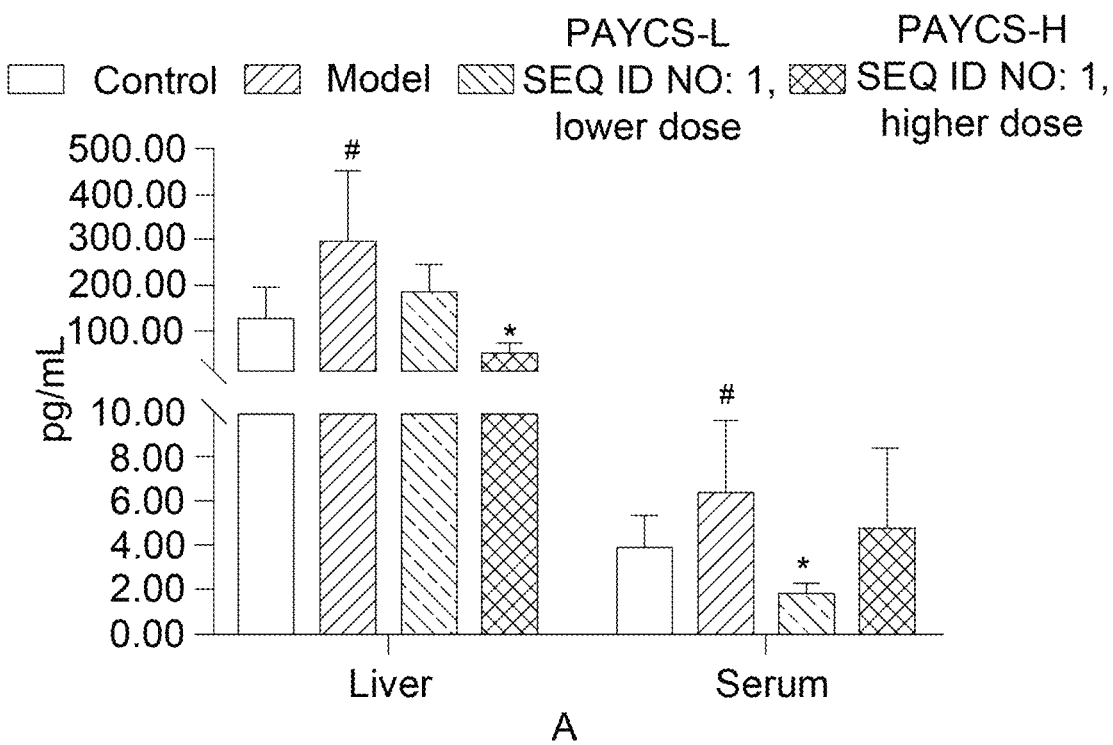
FIG. 3B shows the measurement results of TNF-α content in mouse liver and serum.
Figure 3B:
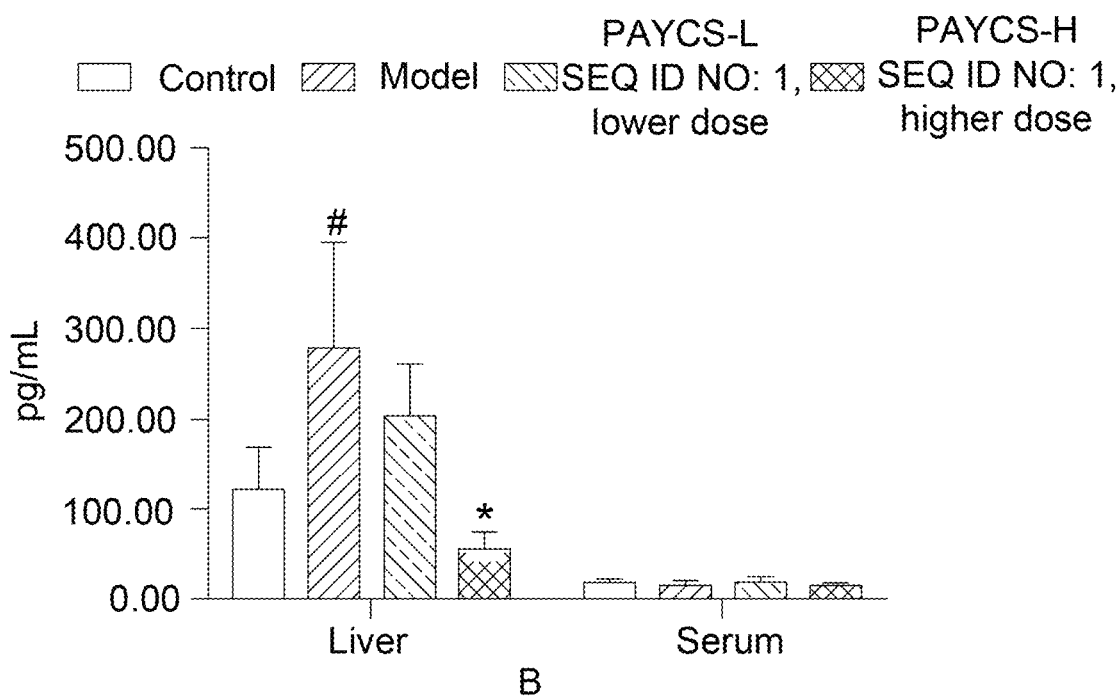
Figure 4A:
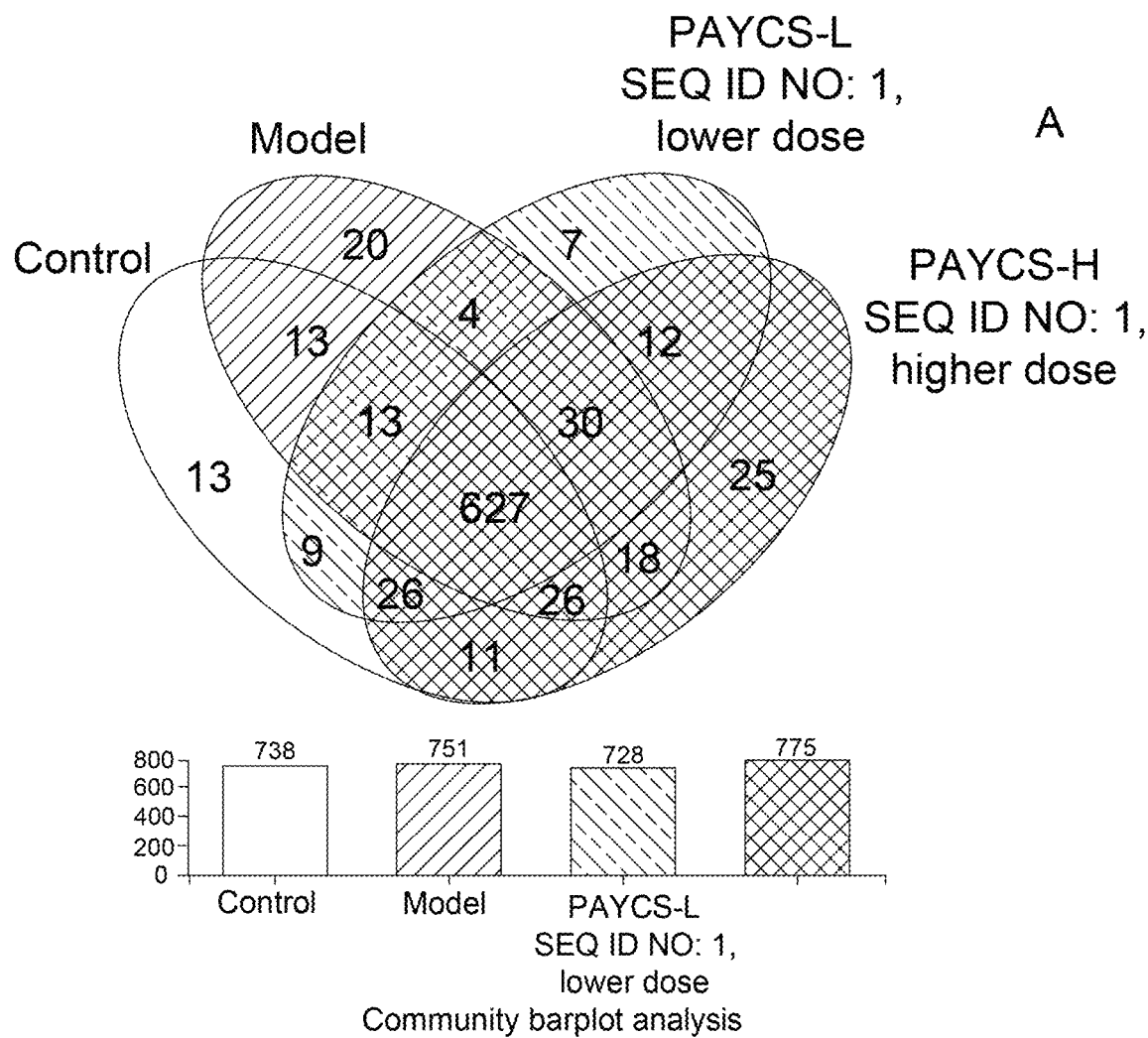
FIG. 4A-FIG. 4F show the effect of PAYCS-L (lower dose of SEQ ID NO: 1) and PAYCS-H (higher dose of SEQ ID NO: 1) on the intestinal microflora in the mice with amnesia induced by scopolamine.
Figure 4B:
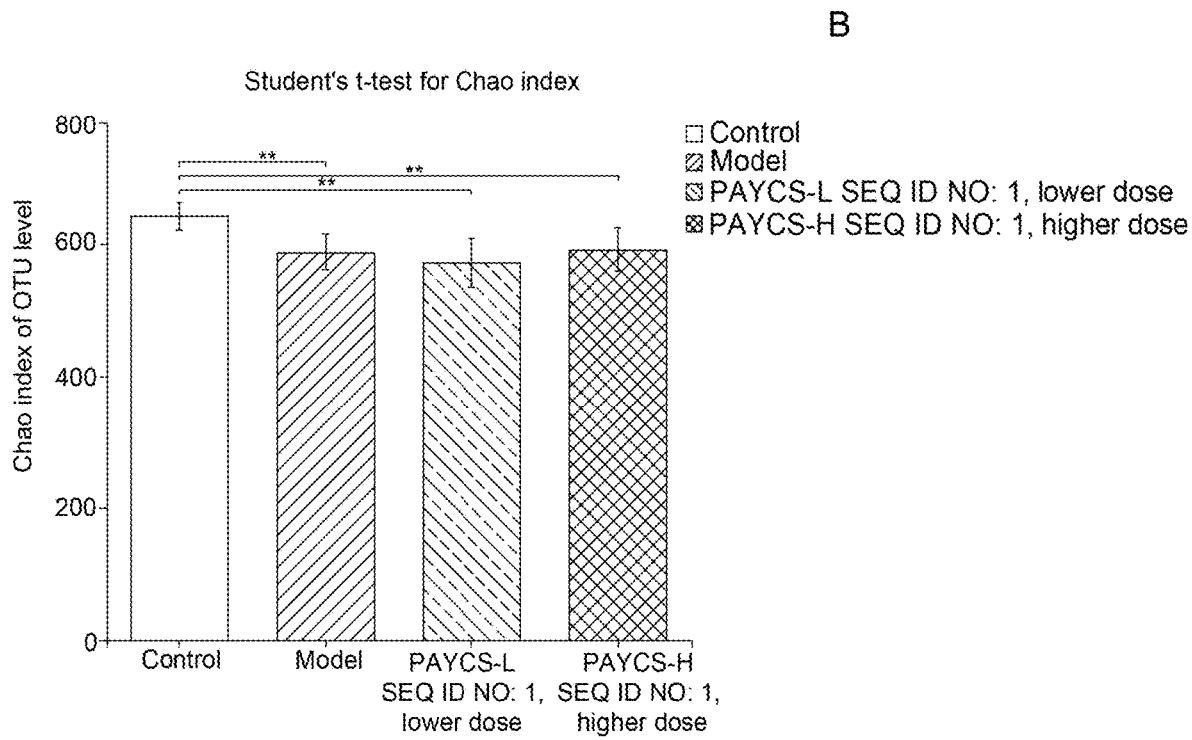
Figure 4C:
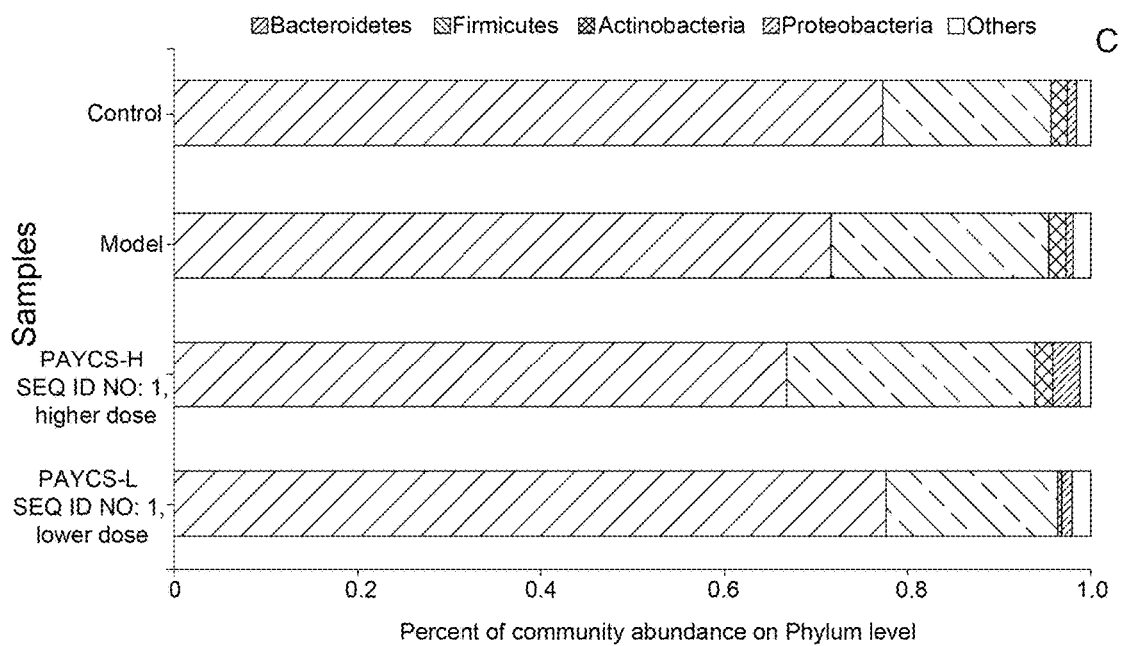
Figure 4D:
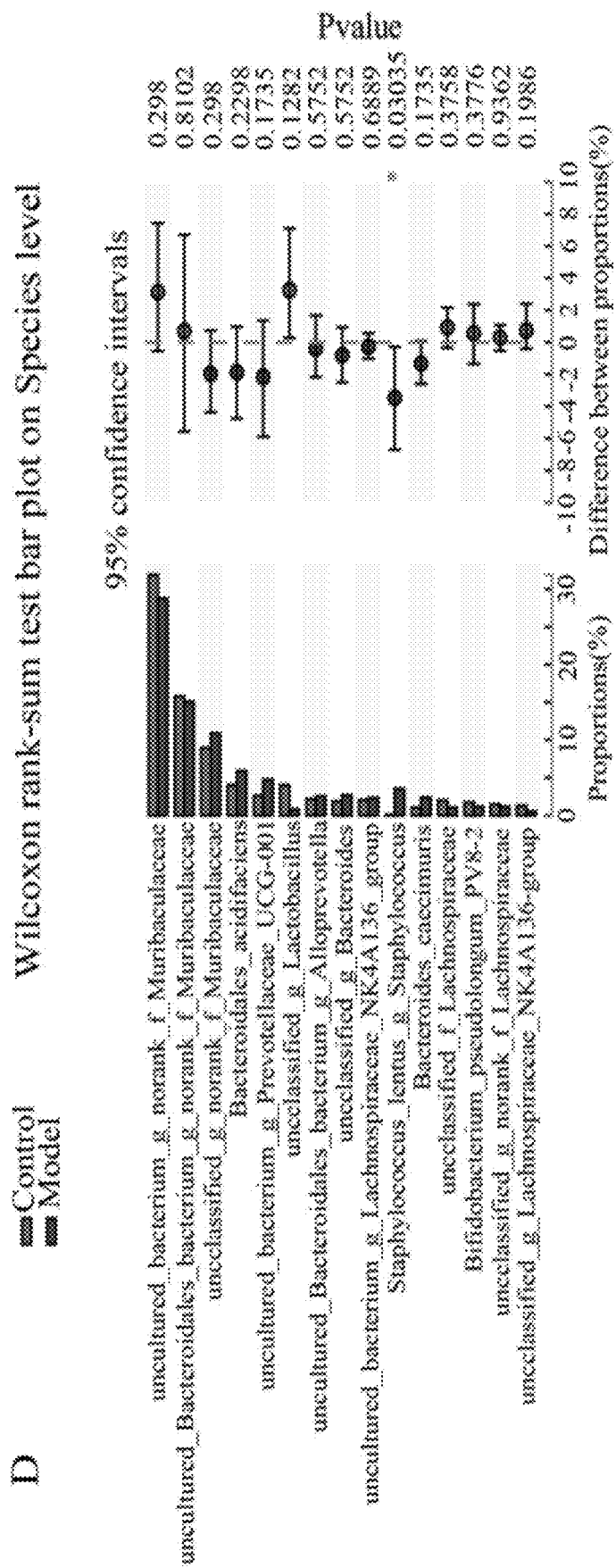
Figure 4E:
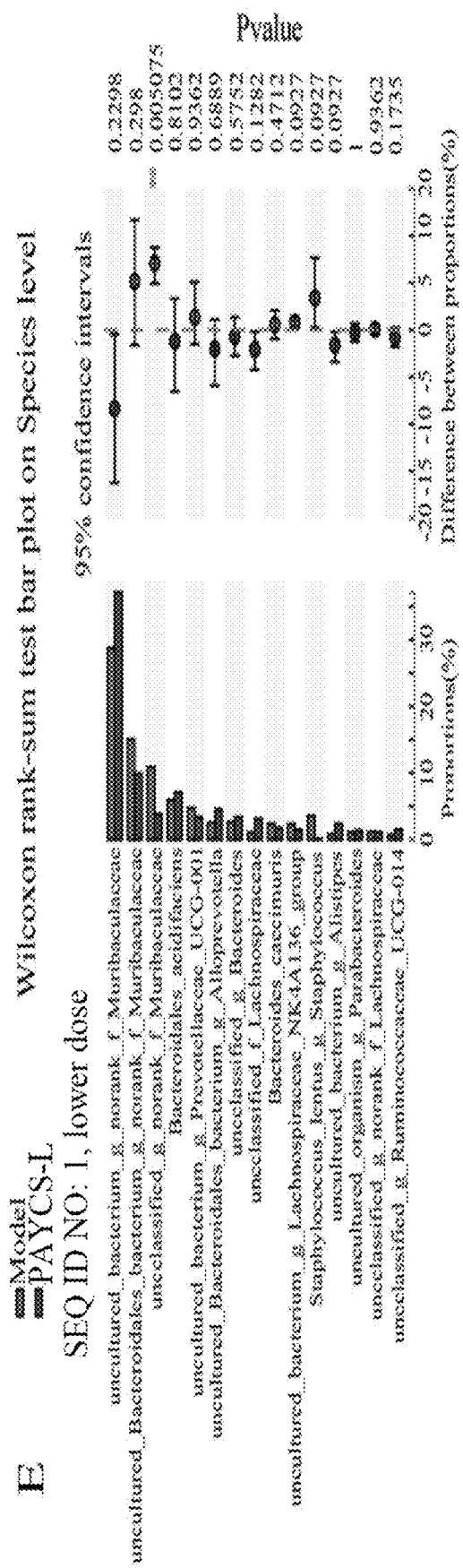
Figure 4F:
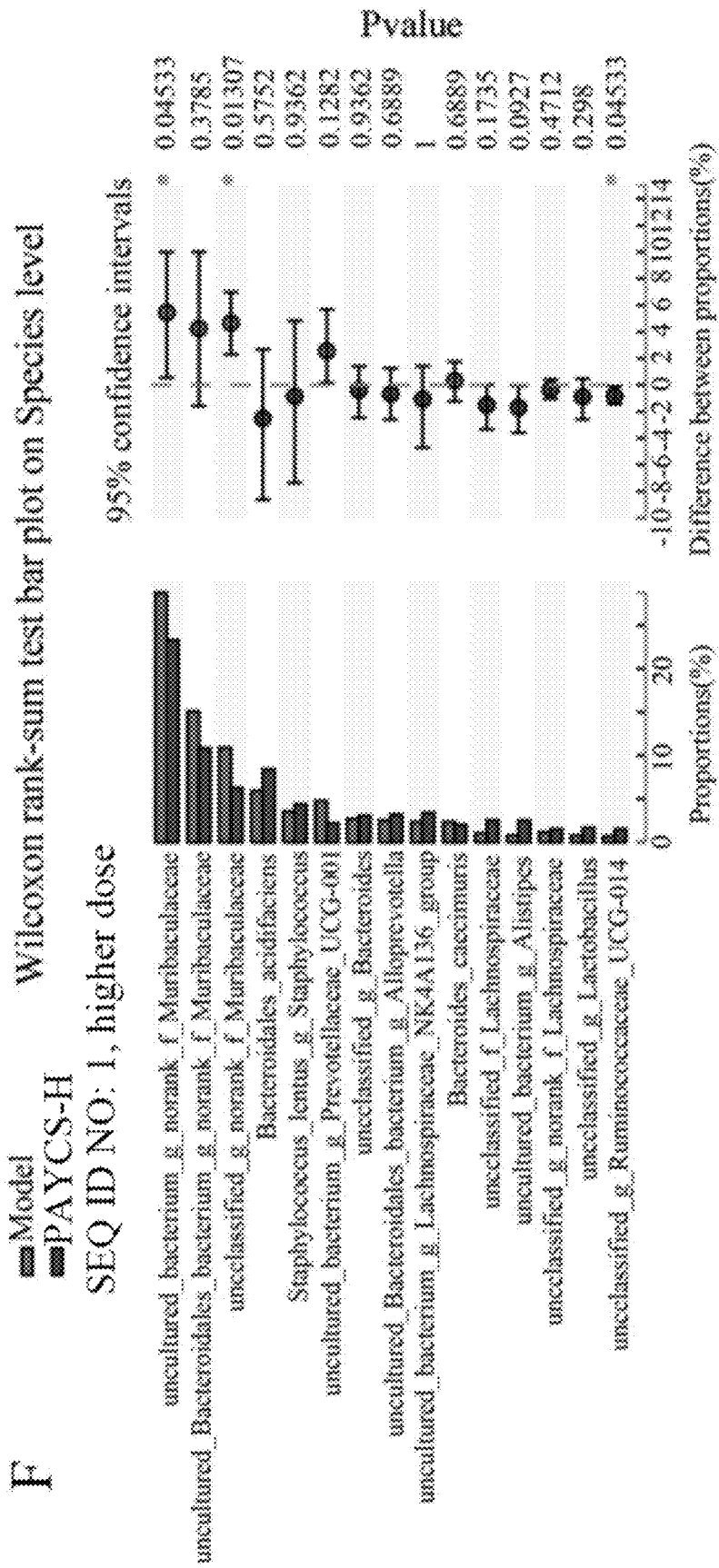

FIG. 3 shows the effect of PAYCS-L (lower dose of SEQ ID NO: 1) and PAYCS-H (higher dose of SEQ ID NO: 1) on the inflammatory indexes in the liver and the serum of mice with amnesia induced by scopolamine, and the contents of IL-1β (FIG. 3A) and TNF-α (FIG. 3B) in mouse liver and serum were determined. #: compared with the control group, P<0.05; *: compared to the model group, P<0.05.

FIG. 4 shows the effect of PAYCS-L (lower dose of SEQ ID NO: 1) and PAYCS-H (higher dose of SEQ ID NO: 1) on the intestinal microflora in the mice with amnesia induced by scopolamine and provides a Venn diagram of a diversity (FIG. 4A) at OTU level, Student's test for Chao index (FIG. 4B), a histogram of community difference and controls and models (FIG. 4D) at the phylum level (FIG. 4C), and the microflora differences between the control and the model, between PYACS-L and the model (FIG. 4E), between PYCS-H and the model (FIG. 4F) at the species level. The symbols * and ** represent P<0.05 and P<0.01, respectively.

Figure 5A:
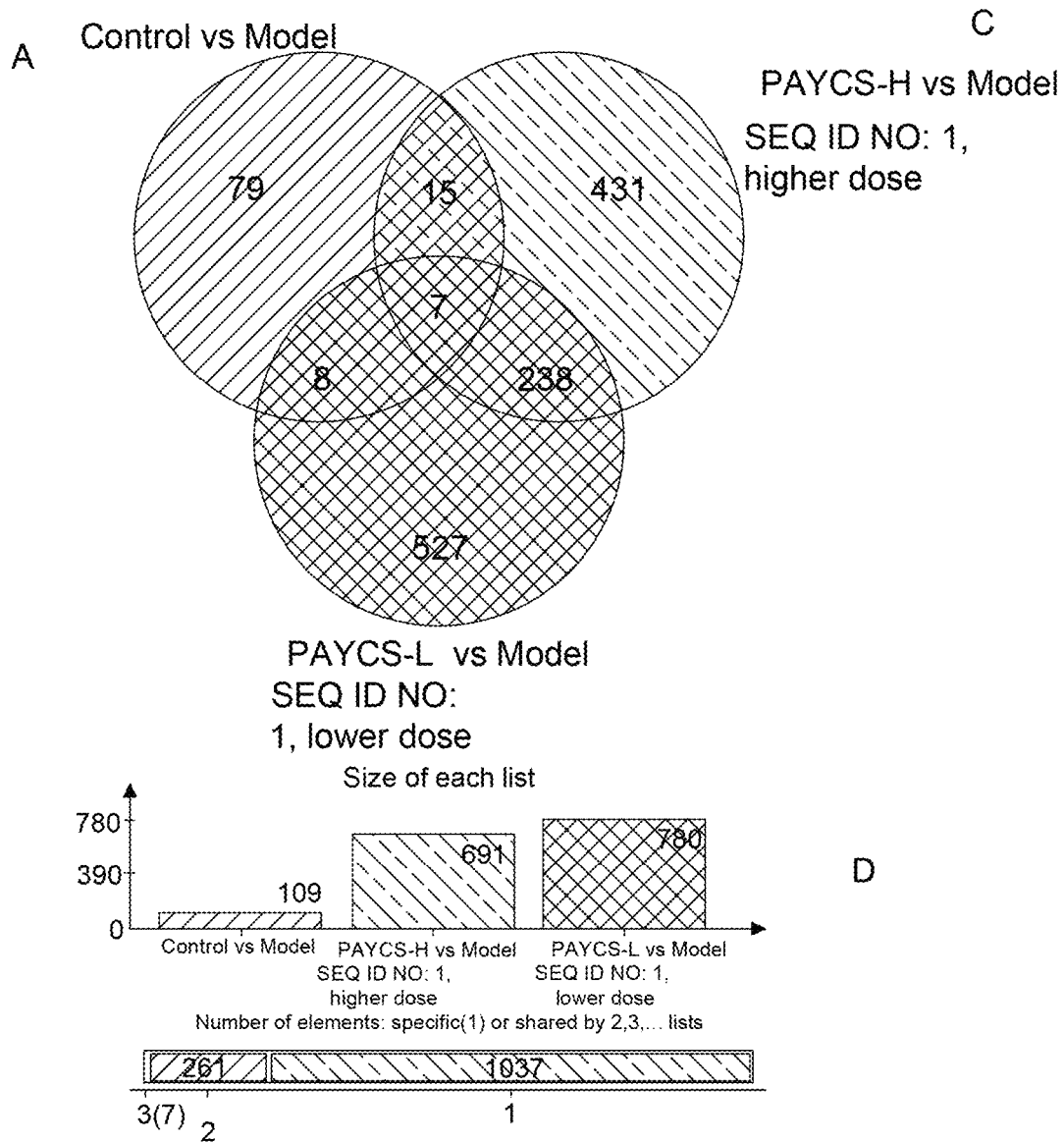
FIG. 5A-FIG. 5E show the effect of PAYCS-L (lower dose of SEQ ID NO: 1) and PAYCS-H (higher dose of SEQ ID NO: 1) on the fecal metabolites of amnesic mice induced by scopolamine.
Figure 5B:
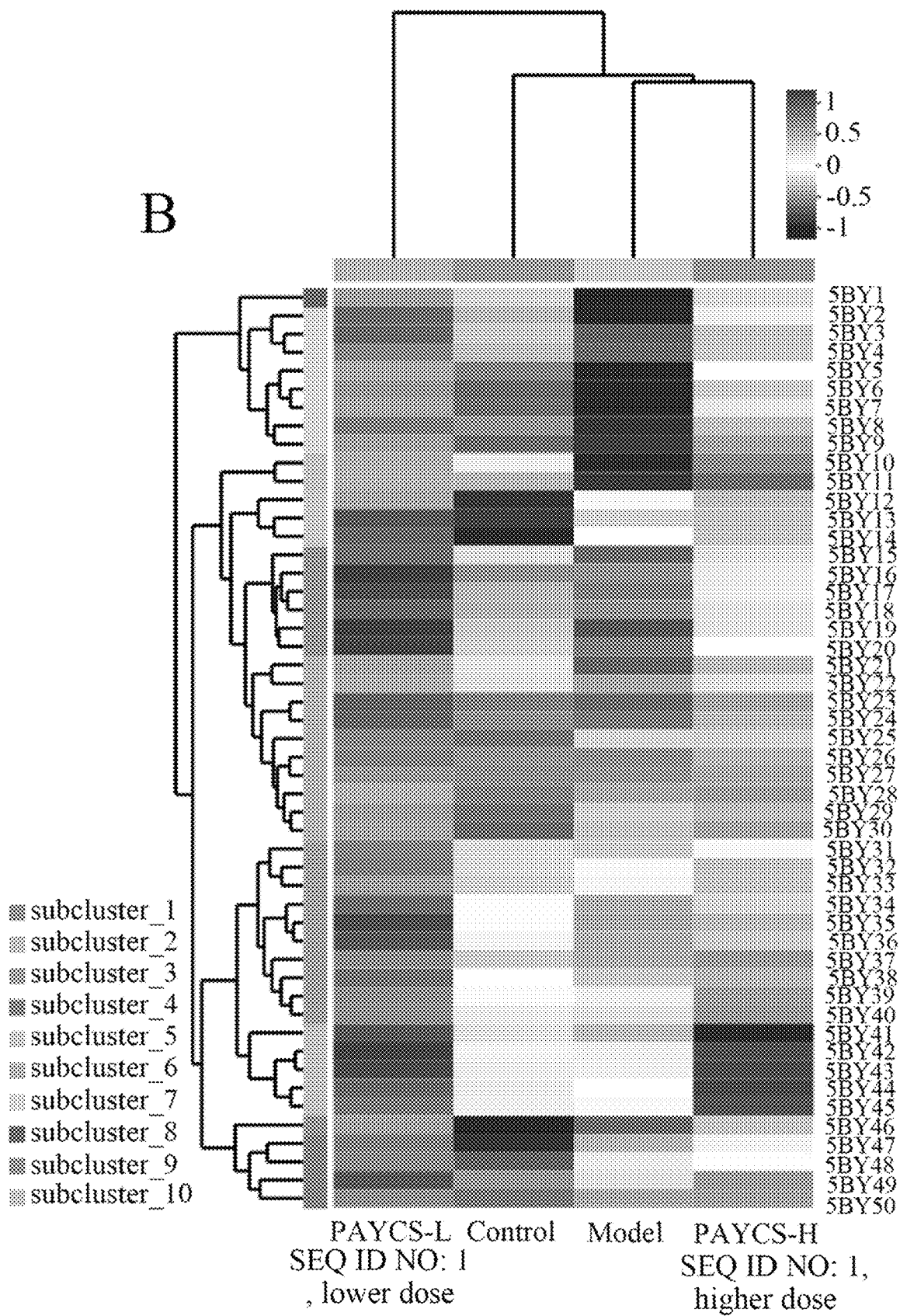
Figure 5C:
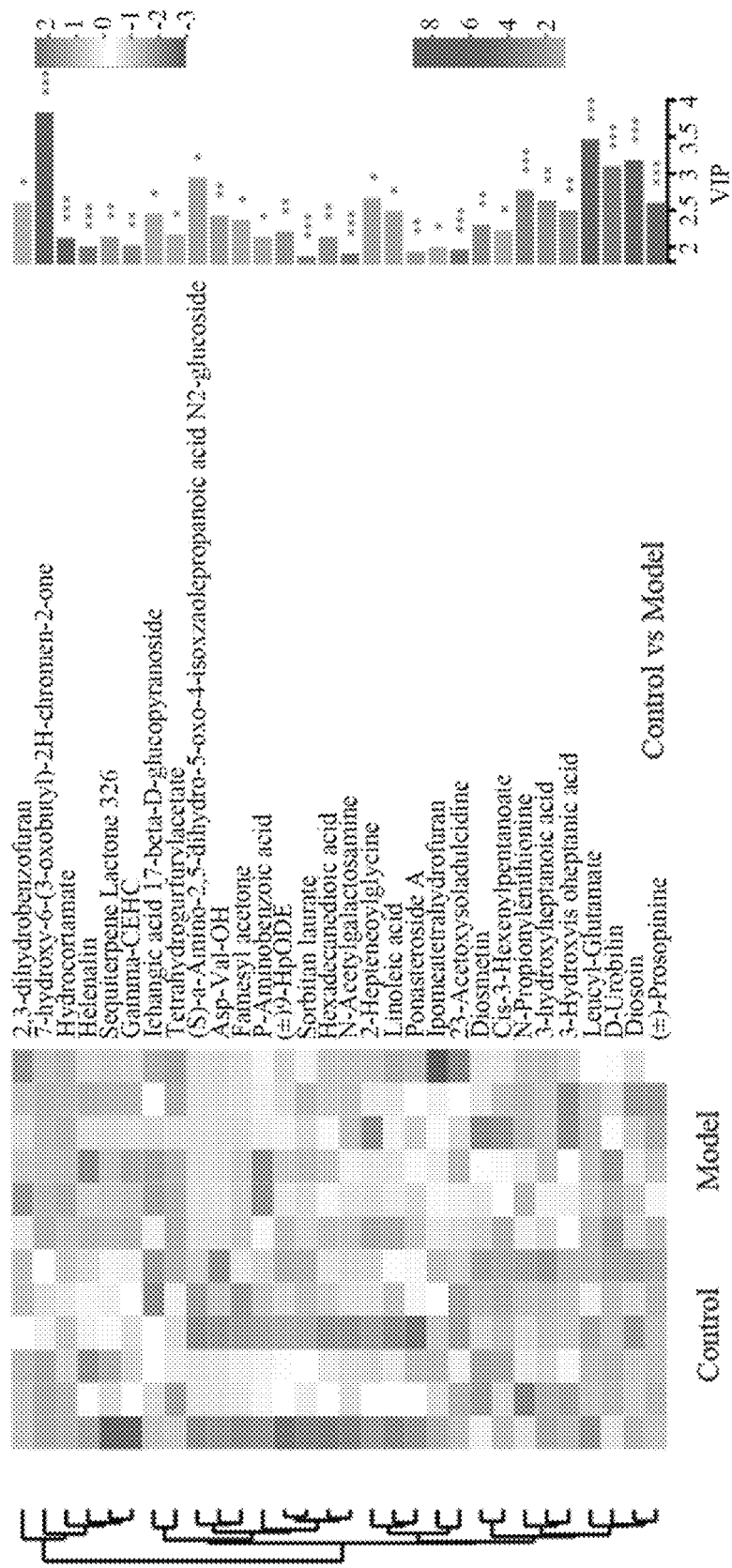
Figure 5D:
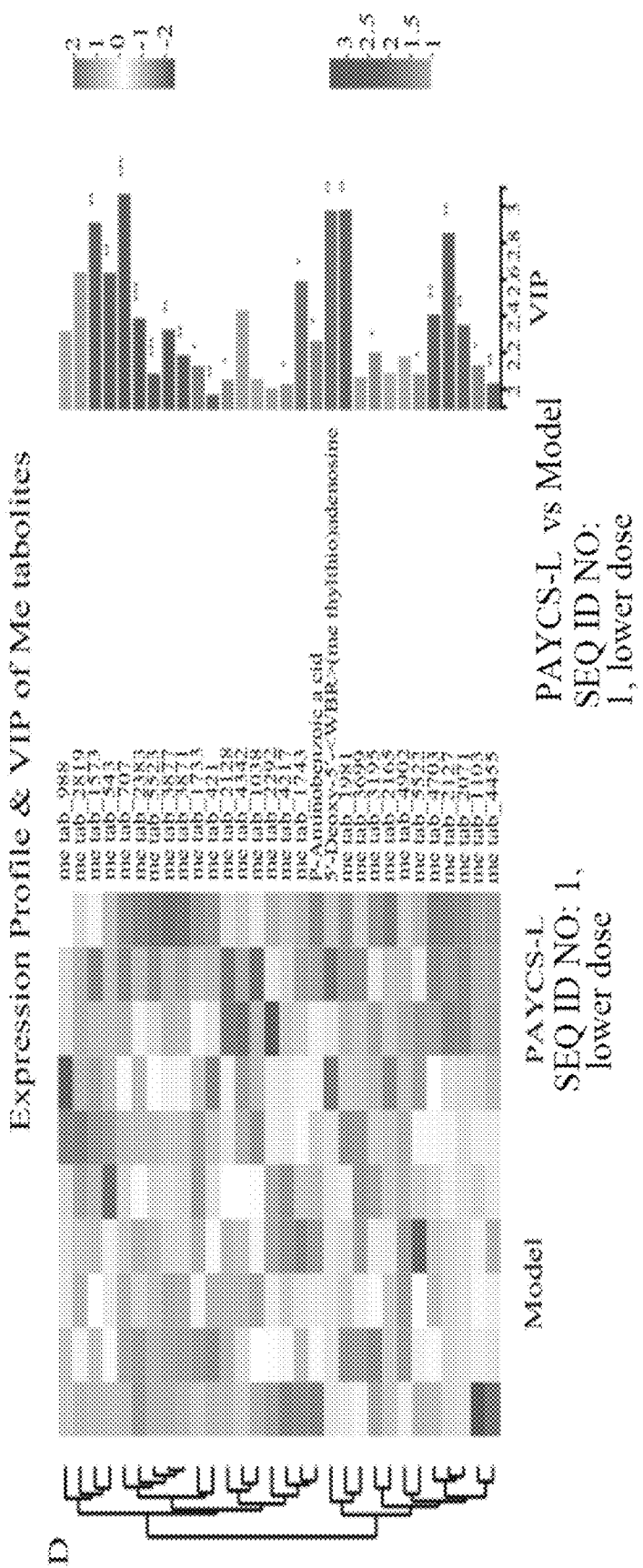
Figure 5E:
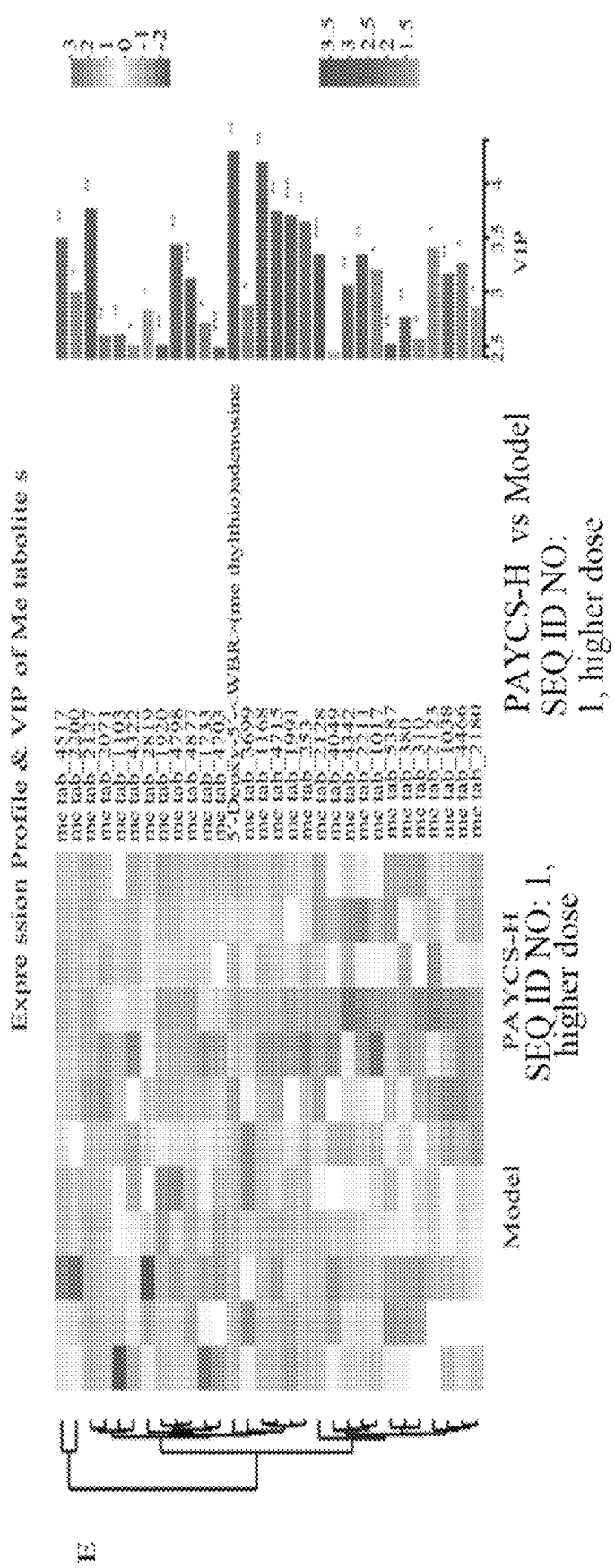

FIG. 5 shows the effect of PAYCS-L (lower dose of SEQ ID NO: 1) and PAYCS-H (higher dose of SEQ ID NO: 1) on fecal metabolites of mice with amnesia induced by scopolamine, showing a Venn diagram (FIG. 5A) of different metabolites, cluster heat map of metabolites (FIG. 5B), control versus model (FIG. 5C), model versus PAYCS-L (lower dose of SEQ ID NO: 1, FIG. 5D), and model versus PAYCS-H (higher dose of SEQ ID NO: 1, FIG. 5E). The scores of variable importance in projection (VIP) for symbol  and symbol * are P<0.05, P<0.01, and P<0.001 respectively.

Figure 6:
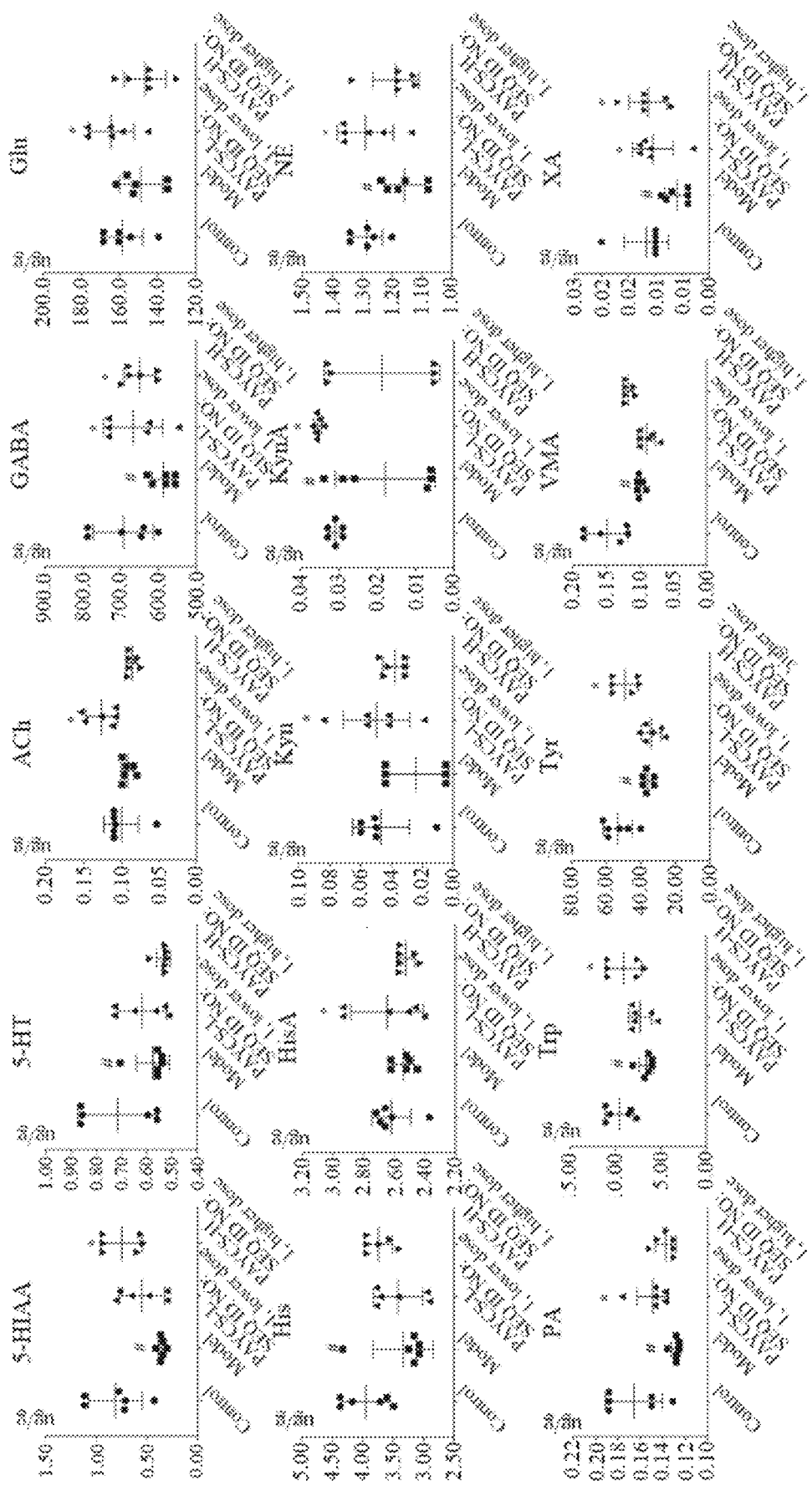
FIG. 6 shows the effect of PAYCS-L (lower dose of SEQ ID NO: 1) and PAYCS-H (higher dose of SEQ ID NO: 1) on neurotransmitters of amnesic mice induced by scopolamine.

FIG. 6 shows the effect of PAYCS-L (lower dose of SEQ ID NO: 1) and PAYCS-H (higher dose of SEQ ID NO: 1) on brain neurotransmitters of mice with amnesia induced by scopolamine. #: compared with the control group, P<0.05; *: compared to the model group, P<0.05.

Figure 7:
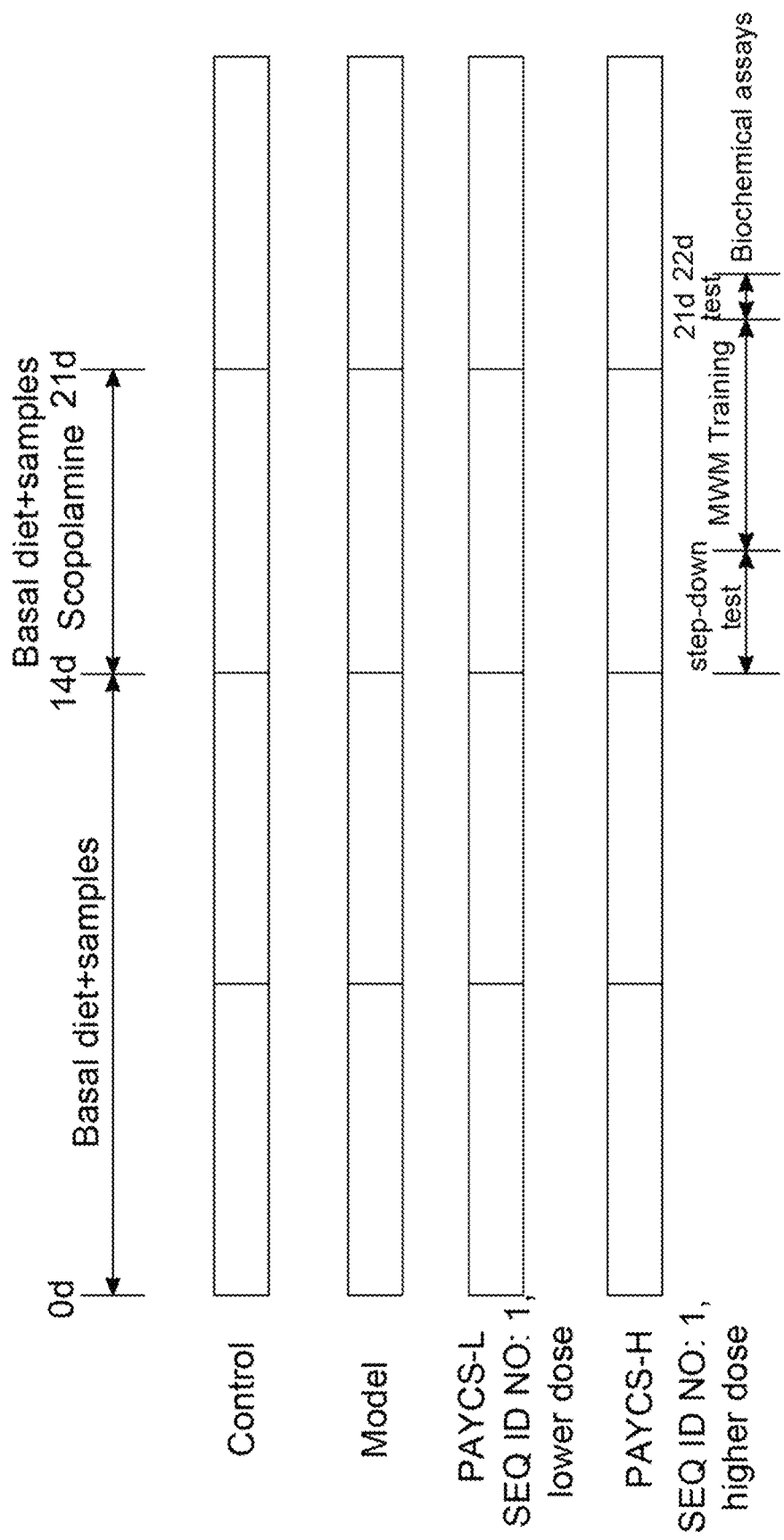
FIG. 7 shows an experiment designed to evaluate the effect of PAYCS-L (lower dose of SEQ ID NO: 1) and PAYCS-H (higher dose of SEQ ID NO: 1) on the learning and memory function of amnesic mice induced by scopolamine.

FIG. 7 is an experiment designed to evaluate the effect of PAYCS-L (lower dose of SEQ ID NO: 1) and PAYCS-H (higher dose of SEQ ID NO: 1) on learning and memory function in mice with amnesia induced by scopolamine.

Figure 8:
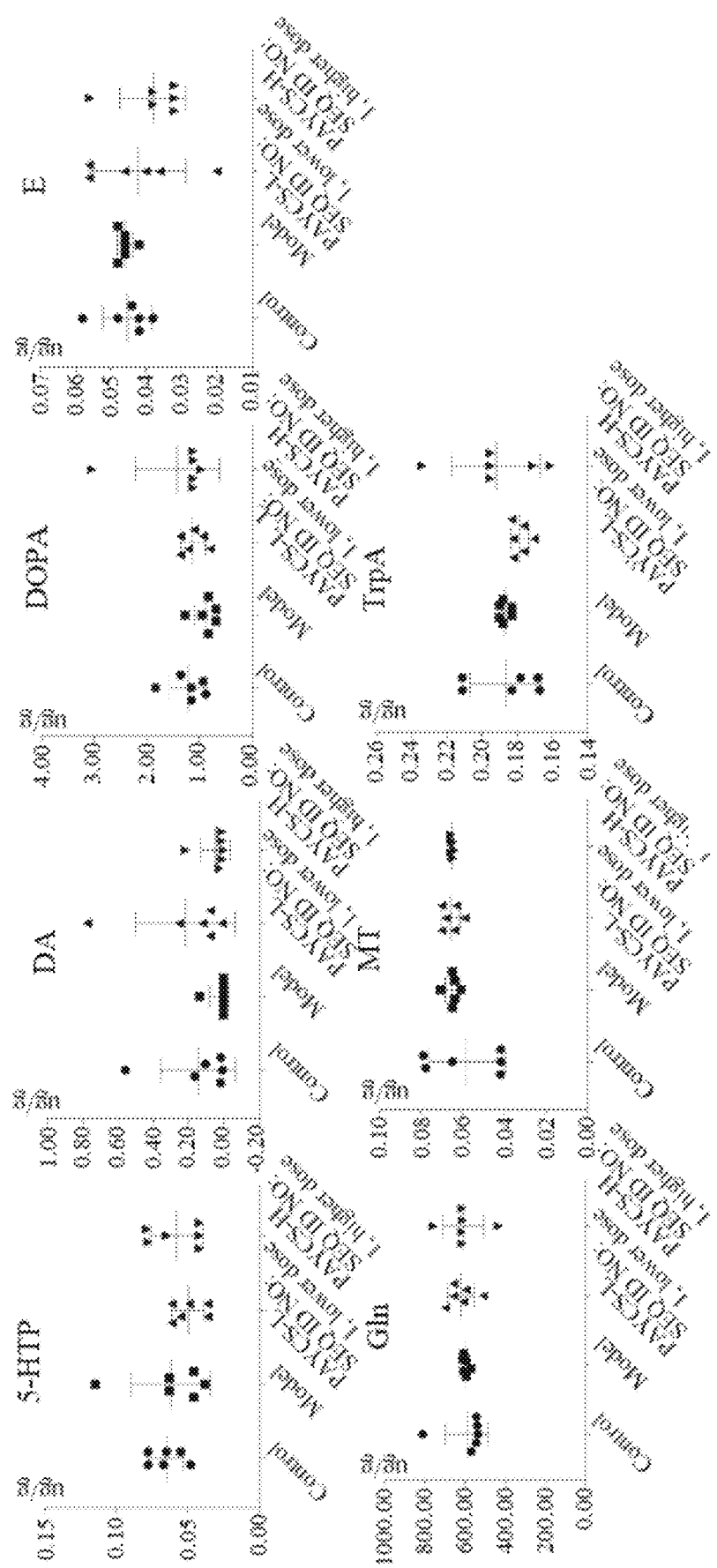
FIG. 8 shows the effect of PAYCS-L (lower dose of SEQ ID NO: 1) and PAYCS-H (higher dose of SEQ ID NO: 1) on neurotransmitters of amnesic mice induced by scopolamine.

FIG. 8 shows the effects of PAYCS-L (lower dose of SEQ ID NO: 1) and PAYCS-H (higher dose of SEQ ID NO: 1) on brain neurotransmitters in mice with amnesia induced by scopolamine.

Figure 9:
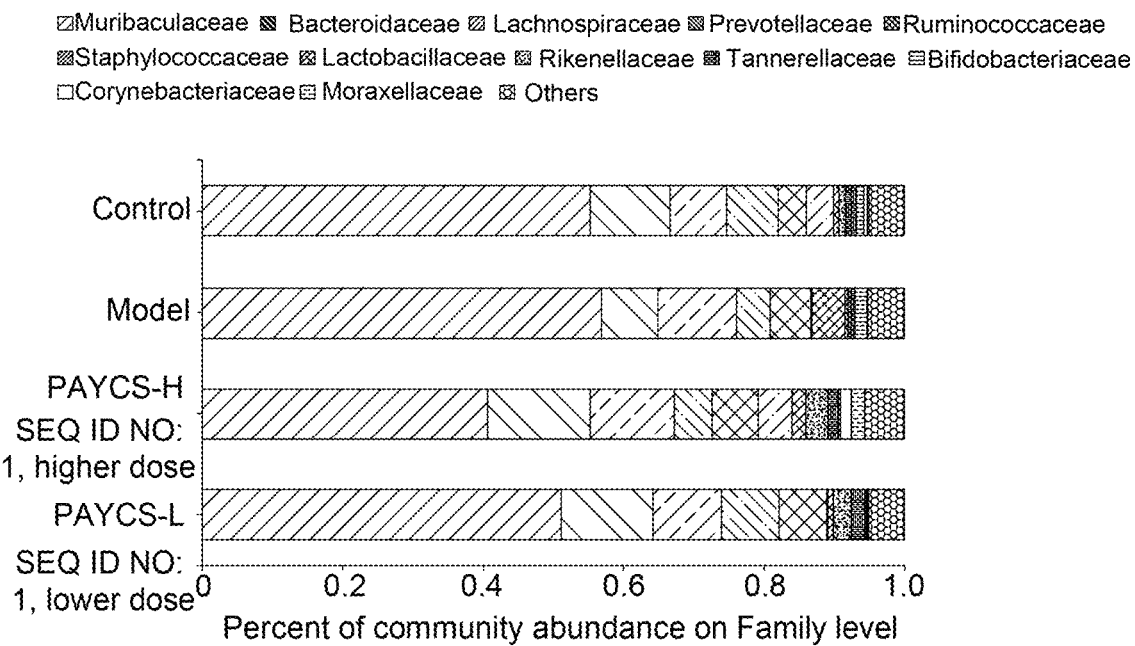
FIG. 9 shows a histogram of community differences at a family level.

FIG. 9 is a histogram of community indifference disparities at the household level.

Figure 10A:
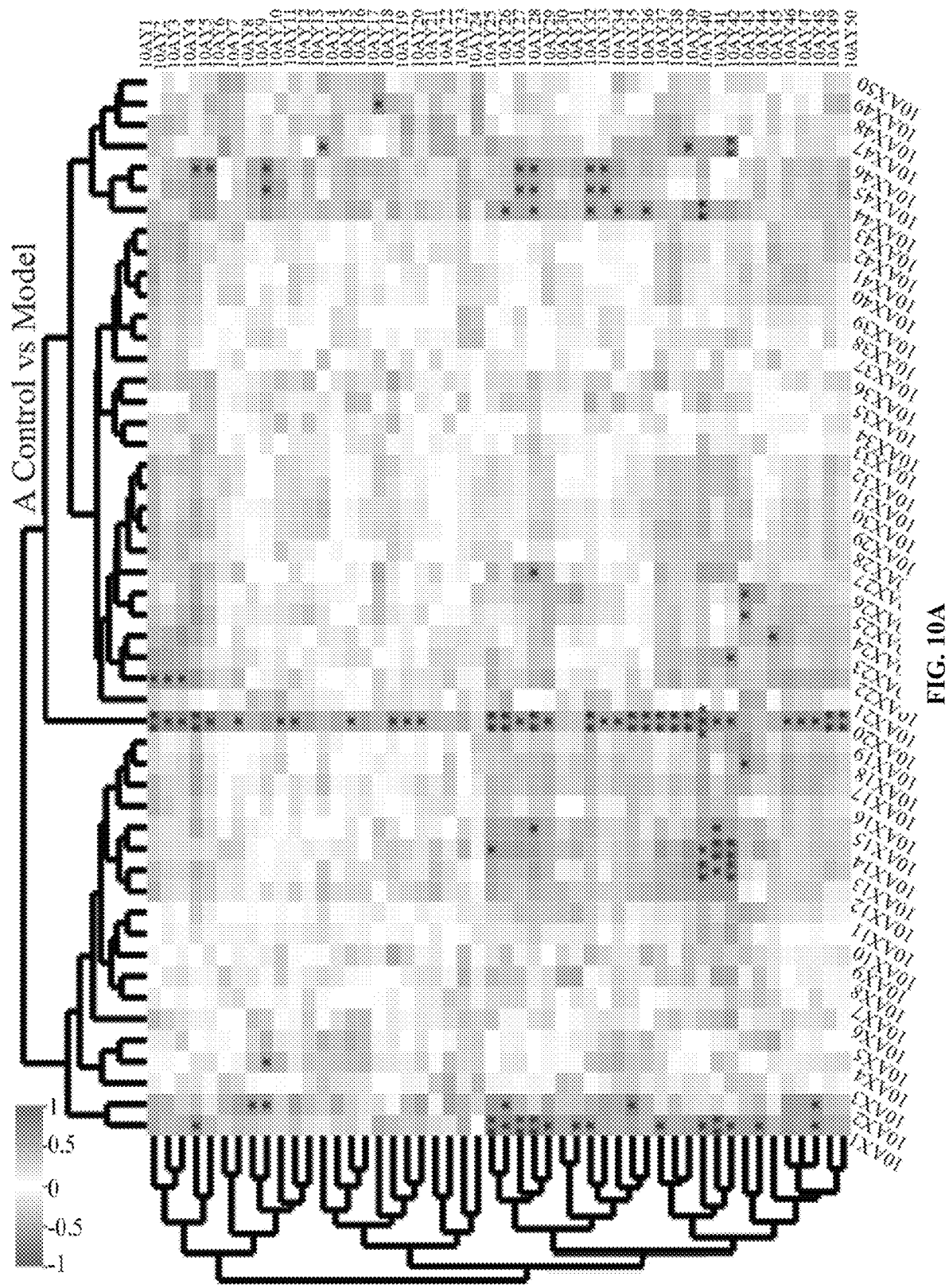
FIG. 10A-FIG. 10C show the correlation analysis between the intestinal flora and the fecal metabolites at a species level.
Figure 10B:
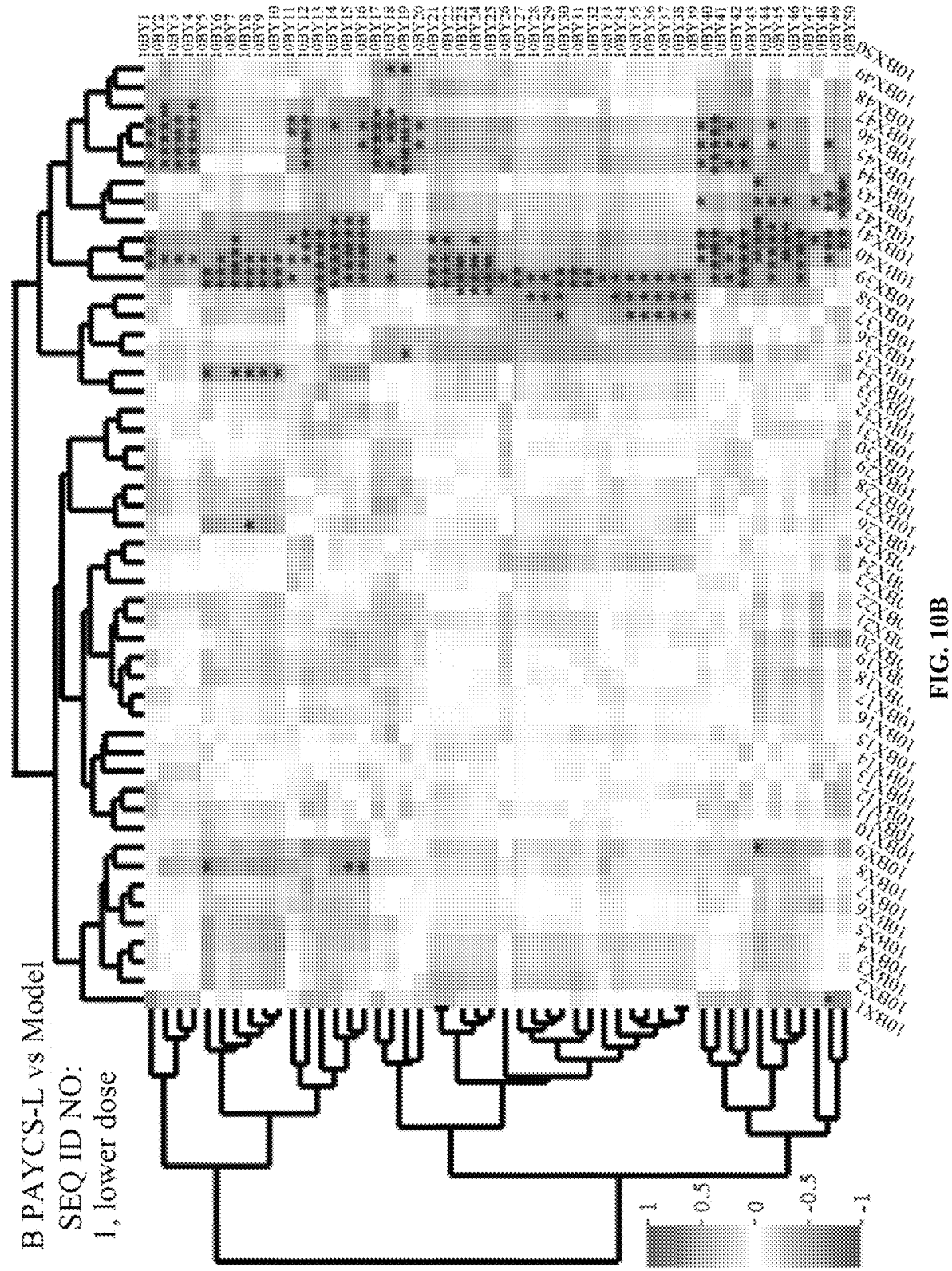
Figure 10C:
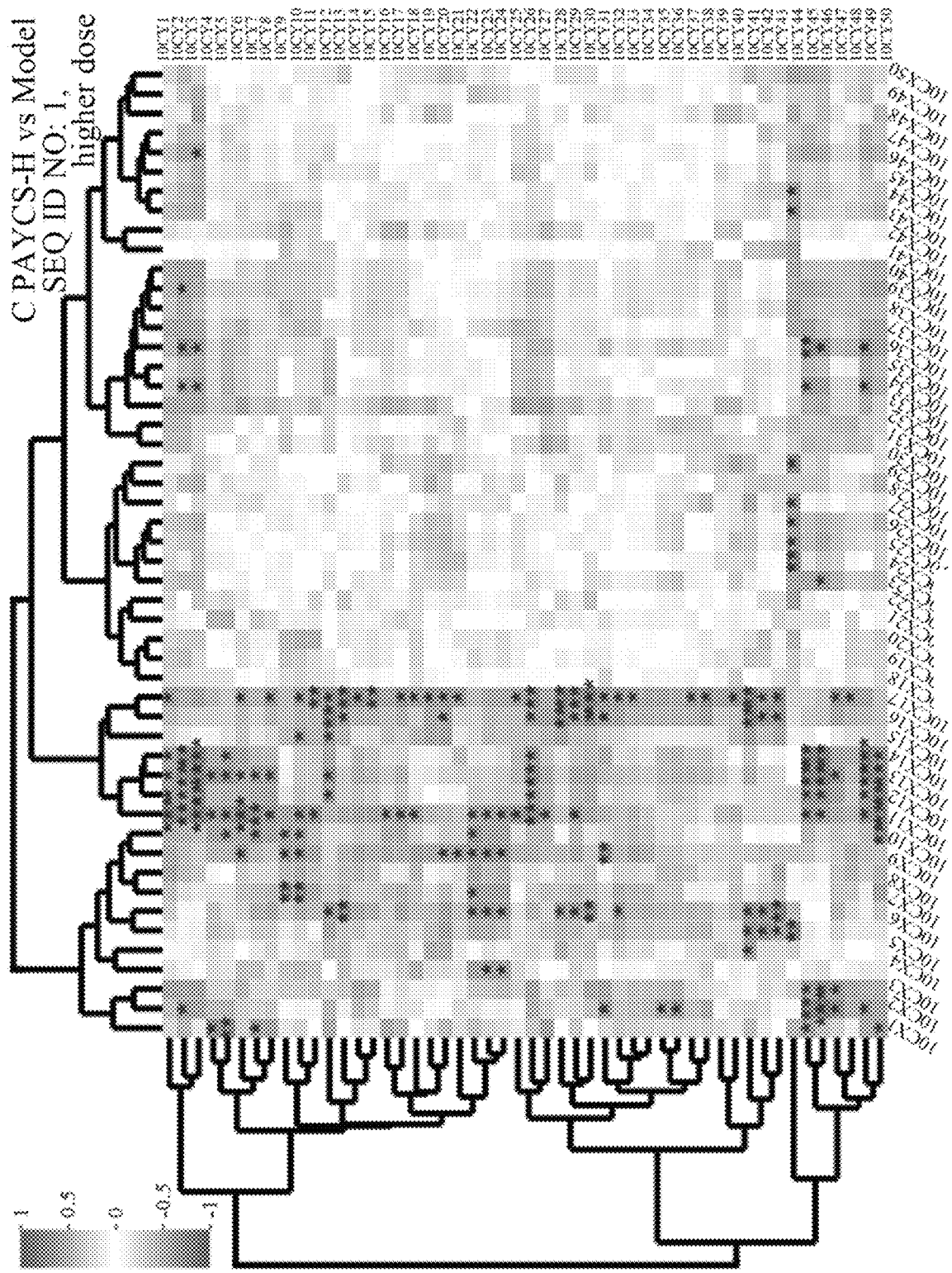

FIG. 10A-FIG. 10C show the correlation analysis of intestinal microorganisms and fecal metabolites at the species level. FIG. 10A: control versus model; FIG. 10B: PAYCS-L (lower dose of SEQ ID NO: 1) versus model; FIG. 10C: PAYCS-H (higher dose of SEQ ID NO: 1) versus model. Symbols *, , and * represent P<0.05, P<0.01, and P<0.001s, respectively.

Figure 11:
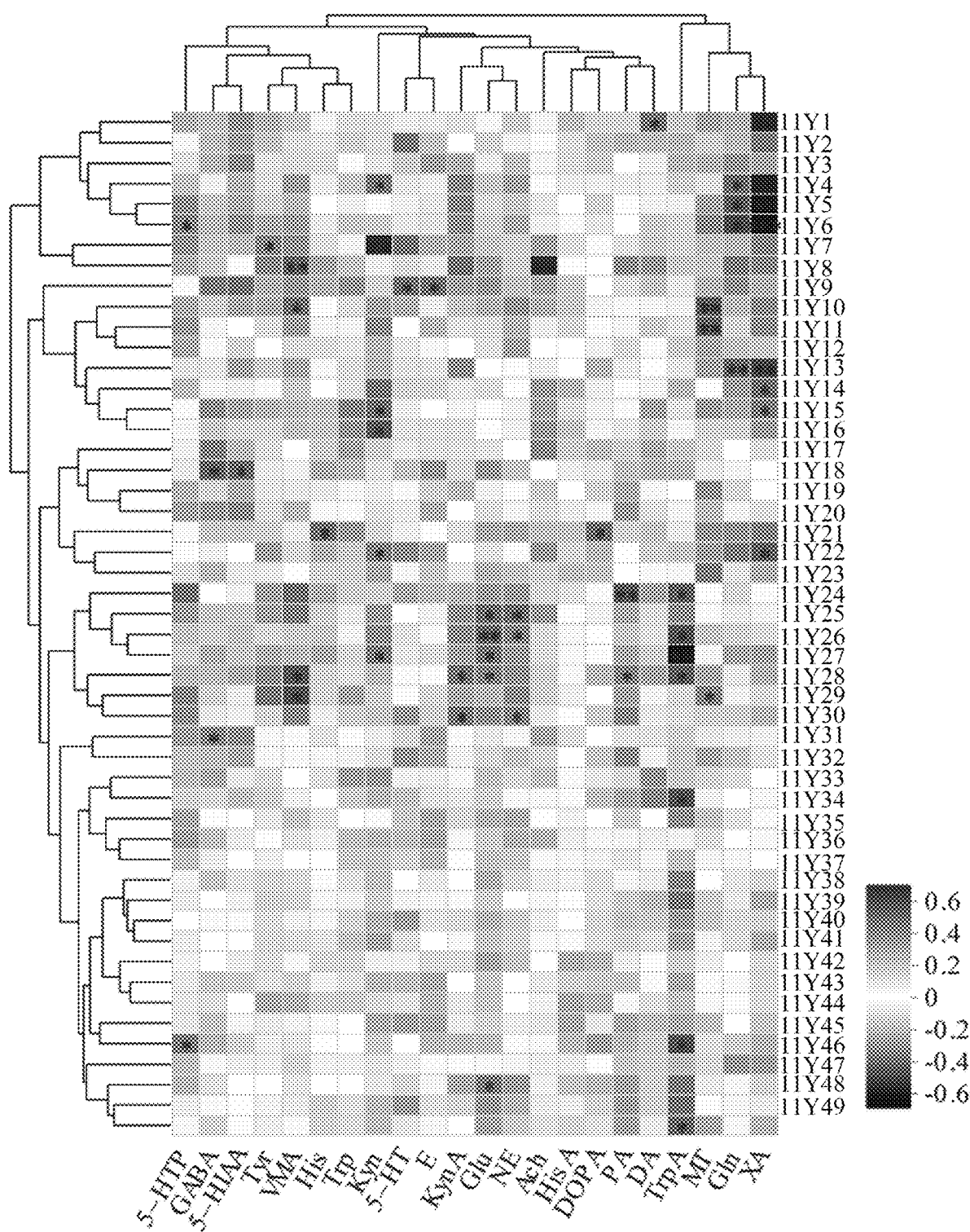
FIG. 11 shows the correlation analysis between the intestinal flora and the neurotransmitters at a genus level.

FIG. 11 shows the correlation analysis of the intestinal microorganism population and the brain neurotransmitters at the genus level. Symbols *, , and * represent P<0.05, P<0.01, and P<0.001, respectively.

Figure 12A:
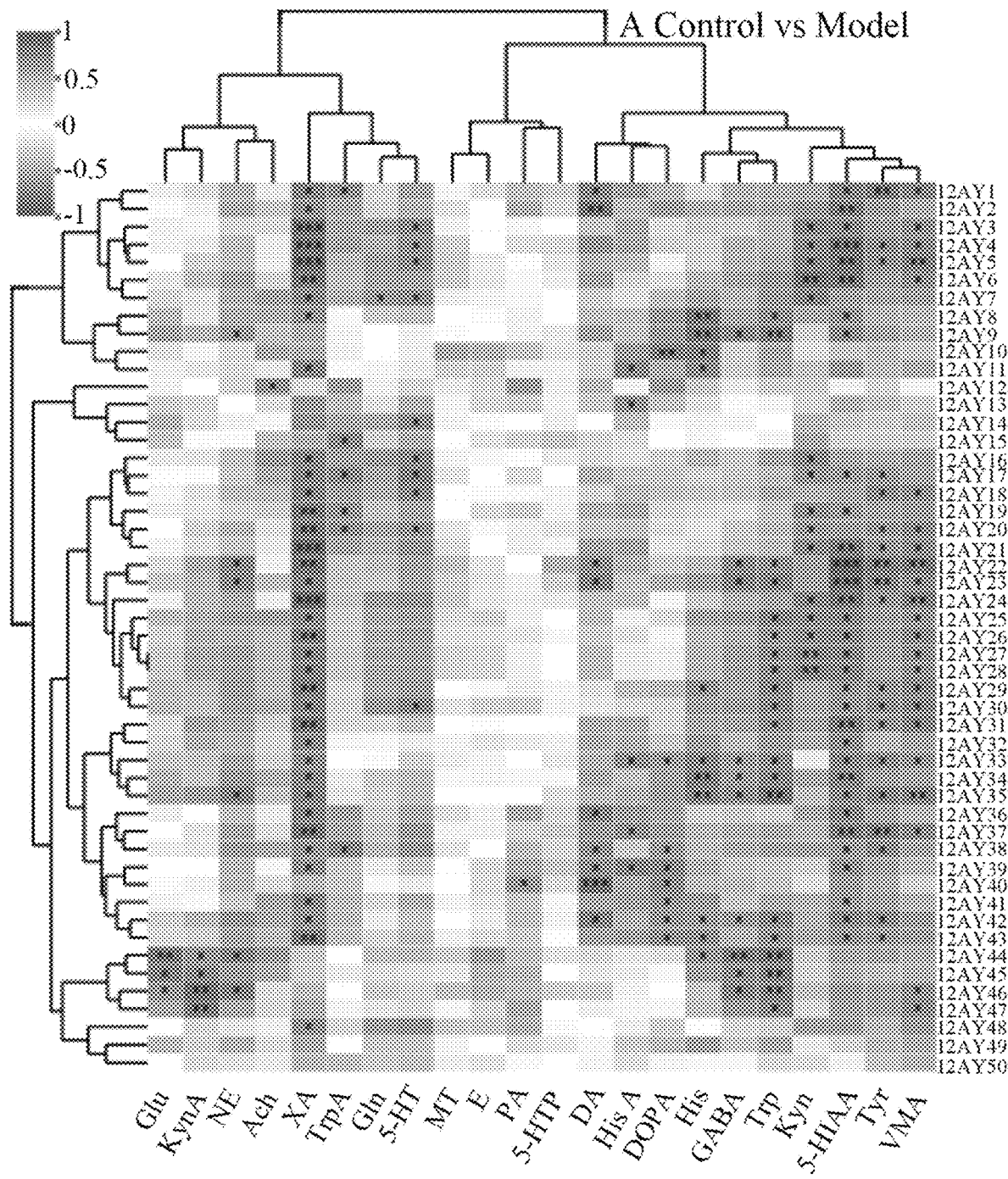
FIG. 12A-FIG. 12C show the correlation analysis between the fecal metabolites and the neurotransmitters.
Figure 12B:
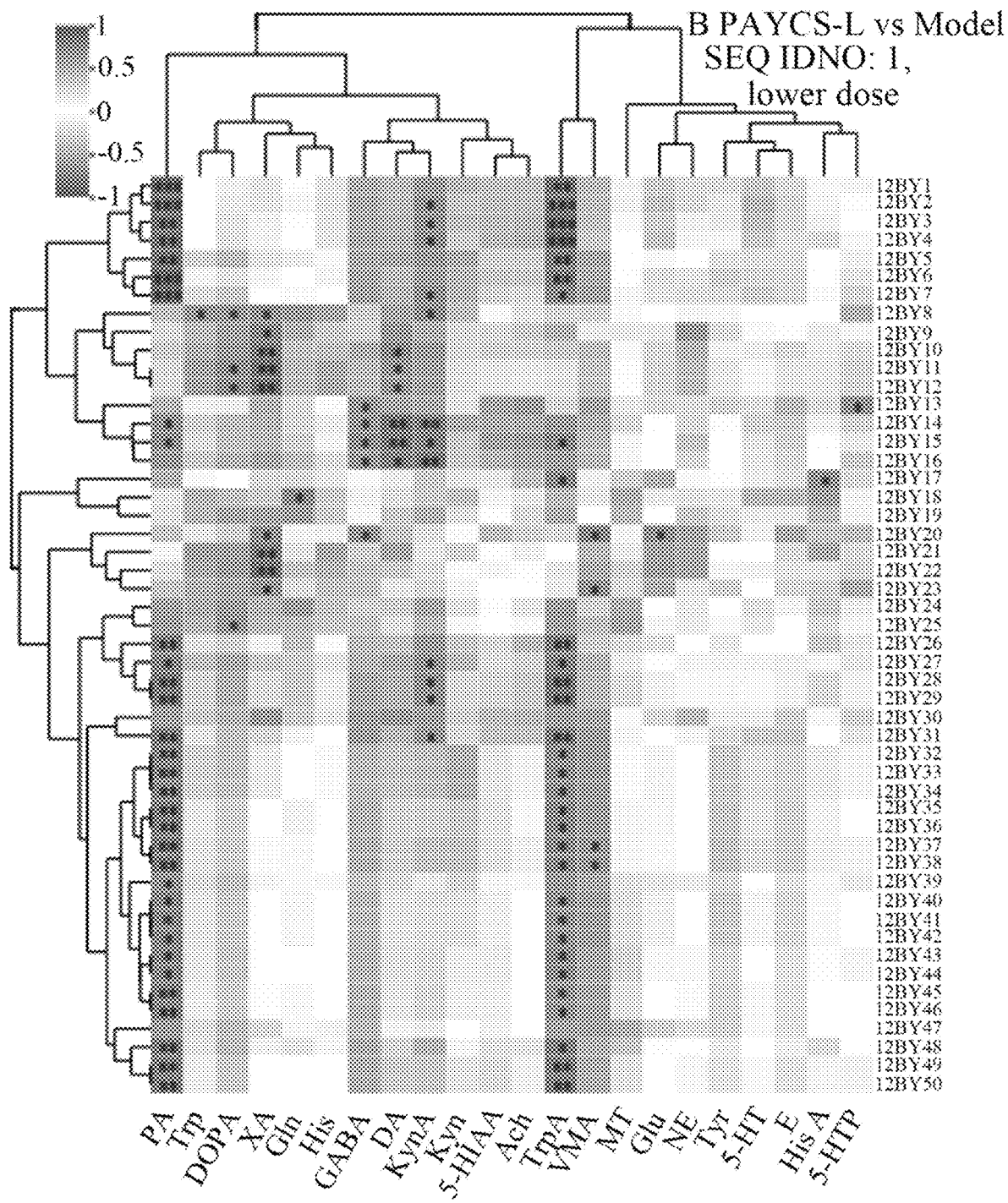
Figure 12C:
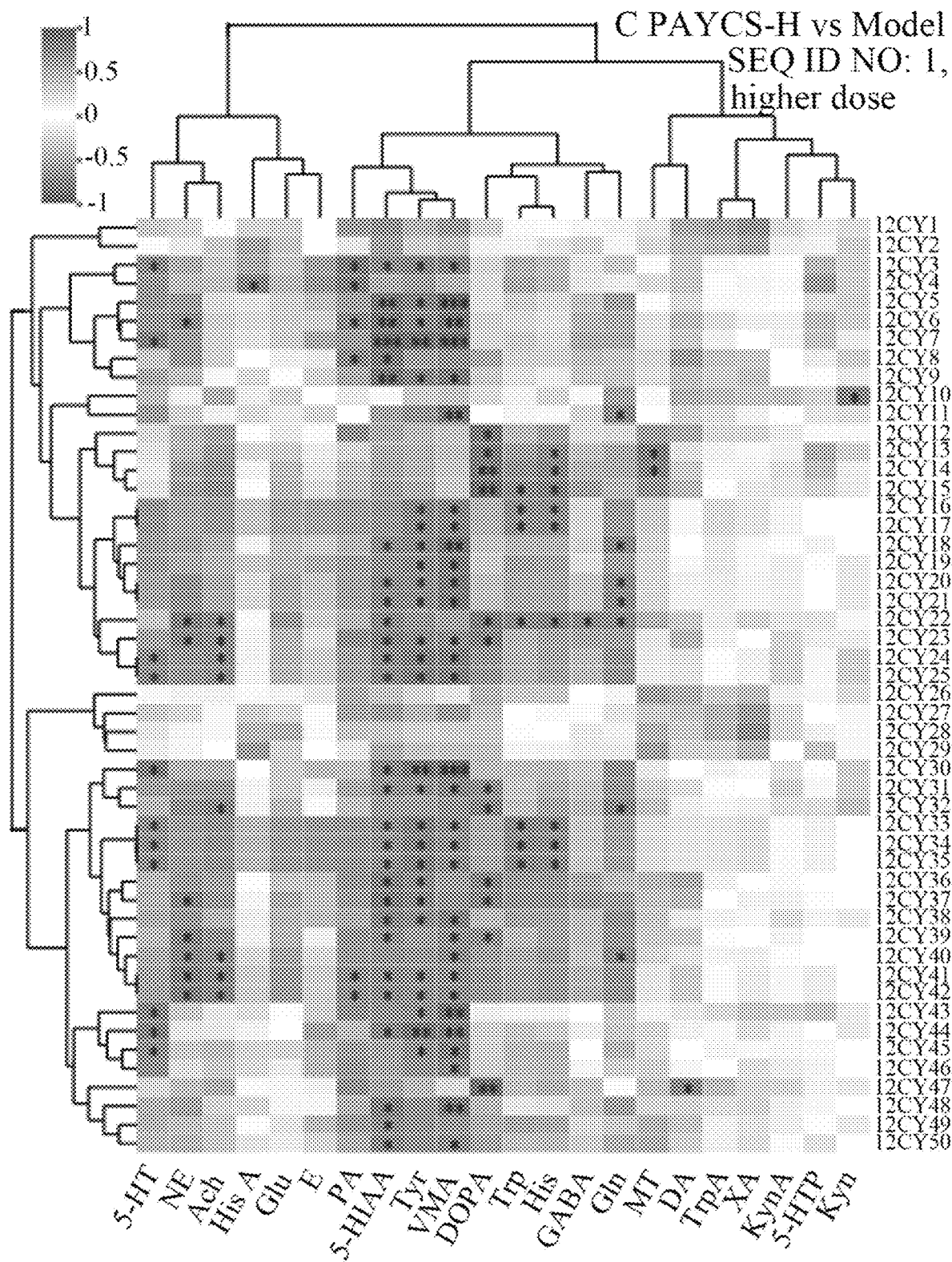

FIG. 12A-FIG. 12C show the correlation analysis of the fecal metabolites and the brain neurotransmitters; FIG. 12A: control versus model; FIG. 12B: PAYCS-L (lower dose of SEQ ID NO: 1) versus model, FIG. 12C: PAYCS-H (higher dose of SEQ ID NO: 1) versus model. Symbols * and ** represent P<0.05, P<0.01, respectively P<0.001.

Described above are only some of the specific embodiments of the present disclosure and the protection scope of the present disclosure is not limited thereto, any person skilled in the art may make any modifications, equivalent substitutions, and improvements within the spirit and principles of the present disclosure, etc., and these modifications or improvements should be deemed to fall within the scope of protection of the present disclosure.

SEQUENCE LISTING

```
Sequence total quantity: 1
SEQ ID NO: 1            moltype = AA  length = 5
FEATURE                 Location/Qualifiers
source                  1..5
                        mol_type = protein
                        note = sequence of the peptide ProAlaTyrCysSer
                        organism = synthetic construct
SEQUENCE: 1
PAYCS                                                                  5
```

What is claimed is:

1. A method for regulating intestinal flora, metabolites, and brain neurotransmitters, comprising a step of administering a peptide to a subject to promote targeted oxidation, improve inflammatory stress, and regulate intestinal microorganism-metabolite-brain neurotransmitter axis; wherein the peptide is PAYCS (SEQ ID NO: 1) and is prepared by using a process including the following conditions for enzymatic hydrolysis by protease:material-liquid ratio 1:3, enzyme dosage 1.3% by weight of the material, pH 7.2, reaction temperature 60° C., and reaction time 50 min; and the conditions for enzymatic hydrolysis using an alkaline protease includes an enzyme dosage of 0.32%, a pH value of 7.3, a reaction temperature of 63° C., and a reaction time of 77 min.

2. The method according to claim 1, wherein the alkaline protease is subjected to a second enzymatic hydrolysis; after the second enzymatic hydrolysis is completed, a heater temperature is adjusted, the pH of the resulting material is adjusted to the desired value using HCl, and glucoamylase is added to degrade the polysaccharide;

upon completion of inactivation of the enzyme, the resulting materials are fully inactivated at 96° C., and a heater, a homogenization pump, and valves are closed, and a cooling water circulating pump is started to promote cooling of the materials; when the temperature drops to 43° C., all the pumps and valves are closed, the discharge valve is opened, and enzymatic hydrolysate is stored in a barrel.

3. The method according to claim 2, wherein a decolorization step is conducted as follows: the enzymatic hydrolysate is centrifuged at 4,100×rpm for 22 min and filtering enzymatic hydrolysate using an 11-kDa ultrafiltration membrane; a supernatant is decolonized with an ultrafiltration membrane, with an inlet pressure of 0.09 MPa, an outlet pressure of 0.07 MPa, and a material temperature of 26° C.; during the whole process, circulating cooling water is used to prevent temperature rise in the material, and a membrane throughput is determined by calculating the volume of outflow liquid within the measurement time.

4. The method according to claim 3, further comprising cleaning of the membrane using a forward cleaning process; firstly, residues in the membrane system are removed with clean water, and a membrane cleaning agent is added to perform circulated cleaning for 61 min; the cleaning solution is removed, and then the membrane system is washed with clean water until eluent becomes clear, contains no foams and the pH value becomes neutral; then a reverse cleaning process is performed as follows: residues in the membrane system are removed with clean water, the ultrafiltration membrane is disassembled and placed and assembled in a direction opposite to the initial direction, and then the ultrafiltration membrane is cleaned using a forward cleaning procedure;

after a spray dryer is cleaned, a dryer and a heater are turned on to dry the water inside the dryer; an atomizer and a feed pump are turned on and the material is sprayed; an inlet temperature is 150° C., a frequency of a nebulizer is set at 370 Hz, and a speed of a peristaltic pump is set at 18 rpm.

5. The method according to claim 1, wherein PAYCS (SEQ ID NO: 1) is administered at a lower dose PAYCS-L or at a higher dose PAYCS-H to an Alzheimer's disease (AD) model mice.

6. The method according to claim 1, wherein the method comprises administering PAYCS-H (higher dose of SEQ ID NO: 1) to improve antioxidant and anti-inflammatory effects.

* * * * *